US009134436B2

(12) United States Patent
Kwak et al.

(10) Patent No.: US 9,134,436 B2
(45) Date of Patent: Sep. 15, 2015

(54) X-RAY APPARATUS AND X-RAY DETECTOR

(71) Applicant: SAMSUNG ELECTRONICS CO., LTD., Suwon-si (KR)

(72) Inventors: Ho-seong Kwak, Seoul (KR); Ig-mo Koo, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/508,714

(22) Filed: Oct. 7, 2014

(65) Prior Publication Data

US 2015/0098551 A1    Apr. 9, 2015

Related U.S. Application Data

(60) Provisional application No. 61/887,607, filed on Oct. 7, 2013.

(30) Foreign Application Priority Data

Oct. 24, 2013 (KR) .................. 10-2013-0127303

(51) Int. Cl.
*H05G 1/56* (2006.01)
*A61B 6/08* (2006.01)
(Continued)

(52) U.S. Cl.
CPC .............. *G01T 1/175* (2013.01); *A61B 6/4266* (2013.01); *A61B 6/4283* (2013.01);
(Continued)

(58) Field of Classification Search
CPC .......... A61B 6/08; A61B 6/4266; A61B 6/44; A61B 6/4405; A61B 6/4494; A61B 6/46; A61B 6/461; A61B 6/465; A61B 6/467; A61B 6/54; A61B 6/587; H05G 1/56; G06F 19/34; G06F 19/3406; G01T 7/00; G01N 23/083
USPC ............. 378/51, 55, 56, 62, 91, 98, 114–116, 378/162–164, 189, 204–206, 210, 98.5, 378/98.8; 250/491.1, 393, 395; 356/3, 3.1, 356/123, 614, 623, 399
See application file for complete search history.

(56) References Cited

U.S. PATENT DOCUMENTS 6,435,716 B1 *   8/2002   Polkus et al. ............... 378/205
6,859,521 B2     2/2005   Spahn
(Continued)

FOREIGN PATENT DOCUMENTS

JP    2003-310591 A    11/2003
JP    2005-193035 A    7/2005
(Continued)

OTHER PUBLICATIONS

Communication dated Feb. 4, 2015 issued by European Patent Office in counterpart European Application No. 14188011.2.
(Continued)

*Primary Examiner* — Anastasia Midkiff
(74) *Attorney, Agent, or Firm* — Sughrue Mion, PLLC

(57) ABSTRACT

An X-ray apparatus includes an X-ray radiation unit configured to radiate X-rays to an object; and a main control unit configured to acquire orientation information of the X-ray radiation unit and orientation information of an X-ray detector and select the X-ray detector based on the orientation information of the X-ray radiation unit and the orientation information of the X-ray detector.

30 Claims, 22 Drawing Sheets

(51) Int. Cl.

| | | |
|---|---|---|
| *G06F 19/00* | (2011.01) | |
| *G01T 1/175* | (2006.01) | |
| *G01N 23/04* | (2006.01) | |
| *H05G 1/30* | (2006.01) | |
| *A61B 6/00* | (2006.01) | |

(52) U.S. Cl.
CPC ............... *A61B 6/4494* (2013.01); *A61B 6/54* (2013.01); *A61B 6/547* (2013.01); *A61B 6/587* (2013.01); *G01N 23/04* (2013.01); *G06F 19/34* (2013.01); *H05G 1/30* (2013.01); *H05G 1/56* (2013.01); *A61B 6/08* (2013.01); *A61B 6/4233* (2013.01); *A61B 6/4405* (2013.01); *A61B 6/461* (2013.01); *A61B 6/465* (2013.01); *A61B 6/467* (2013.01)

(56) References Cited

U.S. PATENT DOCUMENTS

| | | | |
|---|---|---|---|
| 7,187,748 | B2 | 3/2007 | Hoffman |
| 7,426,261 | B2 * | 9/2008 | Spahn ............... 378/98.8 |
| 7,654,739 | B2 * | 2/2010 | Lumma et al. ........... 378/205 |
| 8,243,882 | B2 * | 8/2012 | Jabri et al. ............ 378/116 |
| 2001/0036246 | A1 | 11/2001 | Graumann |
| 2003/0194056 | A1 * | 10/2003 | Spahn ............... 378/205 |
| 2003/0230723 | A1 | 12/2003 | Garrard et al. |
| 2006/0109958 | A1 | 5/2006 | Ertel et al. |
| 2007/0286346 | A1 | 12/2007 | Busch |
| 2009/0257564 | A1 * | 10/2009 | Kito et al. ............ 378/206 |
| 2010/0239070 | A1 * | 9/2010 | Mohr ............... 378/98 |
| 2011/0188633 | A1 | 8/2011 | Ohta et al. |
| 2012/0207274 | A1 | 8/2012 | Yang et al. |

FOREIGN PATENT DOCUMENTS

| | | |
|---|---|---|
| JP | 2006-25828 A | 2/2006 |
| JP | 2010-139454 A | 6/2010 |
| JP | 2012-100843 A | 5/2012 |
| KR | 10-2011-0018042 A | 2/2011 |
| KR | 10-2012-0093677 A | 8/2012 |

OTHER PUBLICATIONS

Written Opinion dated Jan. 20, 2015 issued by International Searching Authority in counterpart International Application No. PCT/KR2014/009452.

International Search Report dated Jan. 20, 2015 issued by International Searching Authority in counterpart International Application No. PCT/KR2014/009452.

* cited by examiner

X-RAY APPARATUS AND X-RAY DETECTOR

CROSS-REFERENCE TO RELATED APPLICATIONS

This application claims the benefit of U.S. Provisional Patent Application No. 61/887,607, filed on Oct. 7, 2013, in the U.S. Patent and Trademark Office, and the benefit of Korean Patent Application No. 2013-0127303, filed on Oct. 24, 2013, in the Korean Intellectual Property Office, the disclosures of which are incorporated herein in their entirety by reference.

BACKGROUND

1. Field

One or more embodiments of the present invention relate to X-ray apparatuses and X-ray detectors, and more particularly, to an X-ray apparatus that selects an X-ray detector to be used for photographing based on the orientation information of the X-ray radiation unit and the orientation information of the X-ray detector, and an X-ray detector.

2. Description of the Related Art

In general, X-rays are electromagnetic waves having a wavelength of 0.01 to 100 Å and can pass through an object. Thus, they may be commonly used in a wide range of applications, such as medical equipment that take images of the inside of a living body and non-destructive testing equipment for industrial use.

X-ray photographing apparatuses using X-rays allow X-rays emitted by an X-ray source to pass through an object, and detect a difference between the intensities of the passed X-rays from an X-ray detector to thereby acquire an X-ray image of the object. X-ray imaging apparatuses are able to easily identify the internal structure of an object based on an X-ray image of the object and to diagnose a disease of the object. X-ray apparatuses are able to easily identify the internal structure of an object by using the principle that the transmission coefficient of X-rays varies depending on the density of the object and the atomic number of an atom of the object. As the wavelength of an X-ray becomes shorter, the transmission coefficient of X-rays increases, and a picture on a screen becomes clearer.

SUMMARY

According to one or more embodiments of the present invention, an X-ray apparatus, comprising an X-ray radiation unit configured to radiate X-rays to an object; and a main control unit configured to acquire orientation information of the X-ray radiation unit and orientation information of an X-ray detector and select the X-ray detector based on the orientation information of the X-ray radiation unit and the orientation information of the X-ray detector.

The apparatus may further include a communication unit configured to transmit a signal generated in the main control unit to the selected X-ray detector.

The signal is generated based on the orientation information of the X-ray radiation unit and the orientation information of the X-ray detector, and is used to prepare the selected X-ray detector to receive a radiated X-ray.

The signal is generated based on a user's input and is used to prepare the selected X-ray detector to receive a radiated X-ray.

When the X-ray detector includes a plurality of X-ray detectors, the main control unit is configured to acquire respective pieces of orientation information of the plurality of X-ray detectors and select at least one X-ray detector from among the plurality of X-ray detectors based on the orientation information of the X-ray radiation unit and the respective pieces of orientation information of the plurality of X-ray detectors.

The apparatus may further include an output unit configured to display information about at least one X-ray detector that is selectable by a user; and an input unit configured to receive a user input for selecting at least one X-ray detector from the information displayed in the output unit, and the main control unit is configured to select at least one X-ray detector, based on the user input.

The main control unit is configured to arrange the information about the at least one X-ray detector according to a predetermined arrangement criterion and control the output unit to display the arranged information.

The communication unit is configured to receive information related to orientation of an X-ray detector from the X-ray detector, and the main control unit is configured to acquire the orientation information of the X-ray detector, based on a reference orientation information of the X-ray detector and the received information.

The reference orientation information is reset when the X-ray detector is coupled to a stand type receptor or a table type receptor.

The main control unit is configured to control orientation of the X-ray radiation unit, based on the orientation information of the selected X-ray detector.

The orientation information of the X-ray radiation unit includes position information of the X-ray radiation unit, and the orientation information of the X-ray detector includes position information of the X-ray detector, wherein the main control unit is configured to select the X-ray detector when a difference between lengths of the position information of the X-ray radiation unit and the position information of the X-ray detector is included in a predetermined range.

The position information of the X-ray radiation unit includes a position vector of the X-ray radiation unit in a global coordinate system expressed as an inertial frame in which an arbitrary location within an X-ray photographing space is the origin, and the position information of the X-ray detector includes a position vector of the X-ray detector in the global coordinate system.

The main control unit is configured to select the X-ray detector, based on a relative vector that is a difference between the position vector of the X-ray radiation unit and the position vector of the X-ray detector.

The orientation information of the X-ray radiation unit includes directional information of the X-ray radiation unit and the orientation information of the X-ray detector includes directional information of the X-ray detector, and the main control unit is configured to select the X-ray detector when a difference between angles of the directional information of the X-ray radiation unit indicating a directional orientation of the X-ray and the directional information of the X-ray detector indicating a facing direction of the X-ray radiation unit, is included in a predetermined range.

The directional information of the X-ray radiation unit includes a first normal vector on a surface of the X-ray radiation unit, and the directional information of the X-ray detector includes a second normal vector on a surface of the X-ray detector.

The main control unit is configured to select the X-ray detector corresponding to the second normal vector when a difference between angles of the first normal vector and the second normal vector is included in a predetermined range.

According to one or more embodiments of the present invention, A wireless X-ray detector, comprising a sensor unit configured to sense orientation of the X-ray detector; a communication unit configured to transmit orientation information of the X-ray detector to an X-ray apparatus; and a detector control unit configured to control the communication unit to transmit the orientation information to the X-ray apparatus and receive a control signal from the X-ray apparatus, and prepare to receive a radiated X-ray based on the control signal.

The detector control unit is configured to acquire the orientation information of the X-ray detector, based on the orientation of the X-ray detector sensed in the sense unit.

The orientation information of the X-ray detector is reset when the wireless X-ray detector is coupled to a stand type receptor or a table type receptor.

The detector control unit is configured to control the communication unit to transmit the orientation information to the X-ray apparatus before receiving the control signal from the X-ray apparatus.

The control signal is generated based on a user's input.

The control signal is generated based on the orientation information of the X-ray radiation unit and the orientation information of the X-ray detector.

The orientation information of the X-ray radiation unit includes position information of the X-ray radiation unit, and the orientation information of the X-ray detector includes position information of the X-ray detector, and the control signal is generated when a difference between lengths of the position information of the X-ray radiation unit and the position information of the X-ray detector is included in a predetermined range.

The position information of the X-ray radiation unit includes a position vector of the X-ray radiation unit in a global coordinate system expressed as an inertial frame in which an arbitrary location within an X-ray photographing space is the origin, and the position information of the X-ray detector includes a position vector of the X-ray detector in the global coordinate system.

The control signal is generated based on a relative vector that is a difference between the position vector of the X-ray radiation unit and the position vector of the X-ray detector.

The orientation information of the X-ray radiation unit includes directional information of the X-ray radiation unit and the orientation information of the X-ray detector includes directional information of the X-ray detector, and the control signal is generated when a difference between angles of the directional information of the X-ray radiation unit indicating a directional orientation of the X-ray and the directional information of the X-ray detector indicating a facing direction of the X-ray radiation unit, is included in a predetermined range.

The directional information of the X-ray radiation unit includes a first normal vector on a surface of the X-ray radiation unit, and the directional information of the X-ray detector includes a second normal vector on a surface of the X-ray detector.

The control signal is generated when a difference between angles of the first normal vector and the second normal vector is included in a predetermined range.

According to one or more embodiments of the present invention, An X-ray apparatus, comprising an X-ray radiation unit configured to radiate X-rays to an object; and a main control unit configured to acquire orientation information of the X-ray radiation unit and orientation information of an X-ray detector and determine whether the X-ray radiation unit faces the X-ray detector.

The orientation information of an X-ray detector is received from the X-ray detector that sense orientation of the X-ray detector and acquire the orientation information of the X-ray detector based on the orientation of the X-ray detector.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

Although general terms widely used at present were selected for describing the present invention in consideration of the functions thereof, these general terms may vary according to intentions of one of ordinary skill in the art, case precedents, the advent of new technologies, and the like. Terms arbitrarily selected by the applicant of the present invention may also be used in a specific case. In this case, their meanings need to be given in the detailed description of the present invention. Hence, the terms must be defined based on their meanings and the contents of the entire specification, not by simply stating the terms.

Throughout the specification, an "image" may refer to multi-dimensional data formed of discrete image elements (e.g., pixels in a two-dimensional (2D) image and voxels in a three-dimensional (3D) image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

In addition, an "object" may be a human, an animal, or a part of a human or animal. For example, the object may include an organ (for example, the liver, the heart, the womb, the brain, breasts, or the abdomen), blood vessels, or a combination thereof. The object may be a phantom. The phantom denotes a material having a volume, a density, and an effective atomic number that are approximately the same as those of a living organism. For example, the phantom may be a spherical phantom having similar properties to those of the human body.

Furthermore, a "user" may be, but is not limited to, a medical expert, for example, a medical doctor, a nurse, a medical laboratory technologist, or a medical imaging expert, or a technician who repairs medical apparatuses.

A "detector" may be used as a synonym for an X-ray detector.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest photographing, simple abdomen photographing, simple skeleton photographing, simple nasal sinuses photographing, simple neck soft tissue photographing, and breast photographing.

Figure 1:
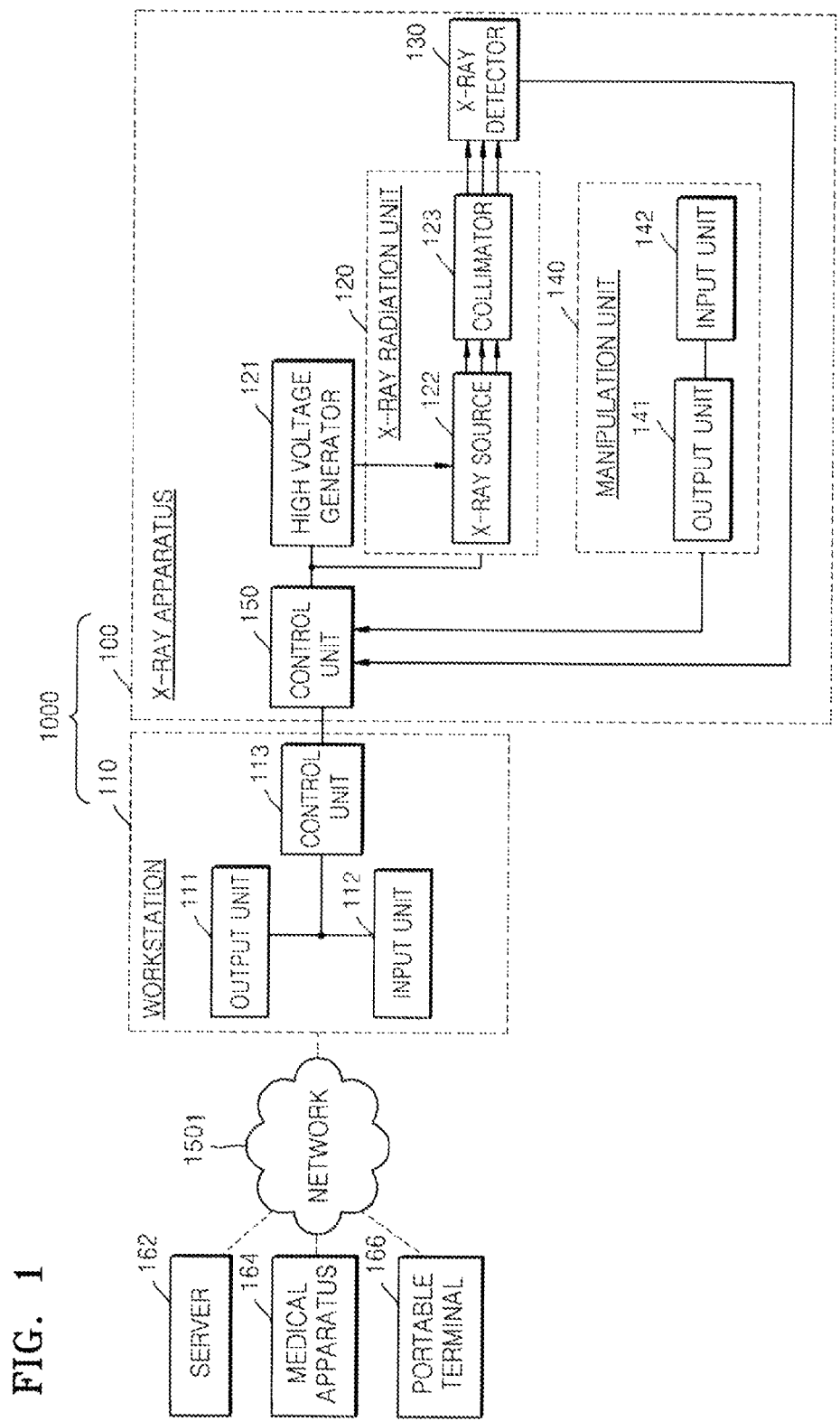
FIG. 1 is a block diagram of an X-ray system.

FIG. 1 is a block diagram of an X-ray system 1000.

Referring to FIG. 1, the X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiation unit 120, a high voltage generator 121, a detector 130, a manipulation unit 140, and a control unit 150. The control unit 150 may control overall operations of the X-ray apparatus 100.

The high voltage generator 121 generates a high voltage for generating X-rays, and applies the high voltage to an X-ray source 122.

The X-ray radiation unit 120 includes the X-ray source 122 receiving the high voltage from the high voltage generator 121 to generate and radiate X-rays, and a collimator 123 for guiding a path of the X-ray radiated from the X-ray source 122 and adjusting an irradiation region radiated by the X-ray.

The X-ray source 122 includes an X-ray tube that may be realized as a vacuum tube diode including a cathode and an anode. An inside of the X-ray tube is set as a high vacuum state of about 10 mmHg, and a filament of the anode is heated to a high temperature to generate thermal electrons. The filament may be a tungsten filament, and a voltage of about 10V and a current of about 3 to 5 A may be applied to an electric wire connected to the filament to heat the filament.

In addition, when a high voltage of about 10 to about 300 kVp is applied between the cathode and the anode, the thermal electrons are accelerated to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, an energy of the X-ray (energy of photon) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 130 detects an X-ray that is radiated from the X-ray radiation unit 120 and has been transmitted through an object. The detector 130 may be a digital detector. The detector 130 may be implemented by using a thin film transistor (TFT) or a charge coupled device (CCD). Although the detector 130 is included in the X-ray apparatus 100 in FIG. 1, the detector 130 may be an X-ray detector that is a separate device capable of being connected to or separated from the X-ray apparatus 100. An X-ray detector according to an embodiment may be a separate device capable of being connected to or separated from an X-ray apparatus.

The X-ray apparatus 100 may further include a manipulation unit 140 for providing a user with an interface for manipulating the X-ray apparatus 100. The manipulation unit 140 may include an output unit 141 and an input unit 142. The input unit 142 may receive from a user a command for manipulating the X-ray apparatus 100 and various types of information related to X-ray photographing. The control unit 150 may control or manipulate the X-ray apparatus 100 according to the information received by the input unit 142. The output unit 141 may output sound representing information related to a photographing operation such as the X-ray radiation under the control of the control unit 150.

The workstation 110 and the X-ray radiation unit 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit 111, an input unit 112, and a control unit 113. The output unit 111 and the input unit 112 provide a user with an interface for manipulating the workstation 110 and the X-ray apparatus 100. The control unit 113 may control the workstation 110 and the X-ray apparatus 100.

The X-ray apparatus 100 may be controlled via the workstation 110 or may be controlled by the control unit 150 included in the X-ray apparatus 100. Accordingly, a user may control the X-ray apparatus 100 via the workstation 110 or may control the X-ray apparatus 100 via the manipulation unit 140 and the control unit 150 included in the X-ray apparatus 100. In other words, a user may remotely control the X-ray apparatus 100 via the workstation 110 or may directly control the X-ray apparatus 100.

Although the control unit 113 of the workstation 110 is separate from the control unit 150 of the X-ray apparatus 100 in FIG. 1, FIG. 1 is only an example. As another example, the control units 113 and 150 may be integrated into a single control unit, and the single control unit may be included in only one of the workstation 110 and the X-ray apparatus 100. Hereinafter, the control units 113 and 150 may denote the single integrated control unit included in the workstation 110 or the X-ray apparatus 100.

The output unit 111 and the input unit 112 of the workstation 110 may provide a user with an interface for manipulating the X-ray apparatus 100, and the output unit 141 and the input unit 142 of the X-ray apparatus 100 may also provide a user with an interface for manipulating the X-ray apparatus 100. Although the workstation 110 and the X-ray radiation unit 100 include the output units 111 and 141, respectively, and the input units 112 and 142, respectively, in FIG. 1, embodiments of the present invention are not limited thereto. Only one of the workstation 110 and the X-ray apparatus 100 may include an output unit or an input unit.

Hereinafter, the input units 112 and 142 may denote the input unit 112 of the workstation 110 or the input unit 142 of the X-ray apparatus 100, and the output units 111 and 141 may denote the output unit 111 of the workstation 110 or the output unit 141 of the X-ray apparatus 100.

Examples of the input units 112 and 142 may include a keyboard, a mouse, a touch screen, a voice recognizer, a fingerprint recognizer, an iris recognizer, and other input devices which are well known to one of ordinary skill in the art. The user may input a command for radiating the X-ray via the input units 112 and 142, and the input units 112 and 142 may include a switch for inputting the command. The switch may be configured so that a radiation command for radiating the X-ray may be input only when the switch is pushed twice.

The switch via which a command for preparing for pre-heating is input, and a switch via which a radiation command for X-ray radiation is input may be separately included.

In other words, when the user pushes the switch, a prepare command for performing a pre-heating operation for X-ray radiation may be input through the switch, and then, when the user pushes the switch once more, the radiation command for performing substantial X-ray radiation may be input through the switch. When the user manipulates the switch as described above, the control units 113 and 150 generate signals corresponding to the commands input through the switch manipulation, that is, a prepare signal, and transmit the generated signals to the high voltage generator 121 generating a high voltage for generating the X-ray.

When the high voltage generator 121 receives the prepare signal from the control units 113 and 150, the high voltage generator 121 starts a pre-heating operation, and when the pre-heating is finished, the high voltage generator 121 outputs a ready signal to the control units 113 and 150. In addition, the detector 130 also needs to prepare to detect the X-ray, and thus the high voltage generator 121 performs the pre-heating operation and the control units 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 transmits a ready signal to the control units 113 and 150. Also, when the high voltage generator 121 receives the prepare signal from the control unit 150, the high voltage generator 121 transmit a prepare signal to the X-ray detector so that the X-ray detector may prepare to detect the X-ray transmitted through the object.

And then, the X-ray detector prepares to detect the X-ray in response to the prepare signal, and when the preparing for the detection is finished, the X-ray detector transmits a ready signal to the high voltage generator 121. In this case, the high voltage generator 121 may transmit the ready signal to the control unit 150.

When the pre-heating operation of the high voltage generator 121 is finished and the detector 130 is ready to detect the X-ray, the control units 113 and 150 transmit a radiation signal to the high voltage generator 121, the high voltage generator 121 generates and applies the high voltage to the X-ray source 122, and the X-ray source 122 radiates the X-ray.

When the control units 113 and 150 transmit the radiation signal to the high voltage generator 121, the control units 113 and 150 may transmit a sound output signal to the output units 111 and 141 so that the output units 111 and 141 output a predetermined sound and the object may recognize the radiation of the X-ray. The output units 111 and 141 may also output a sound representing information related to photographing in addition to the X-ray radiation. In FIG. 1, the output unit 141 is included in the manipulation unit 140; however, the embodiments of the present invention are not limited thereto, and the output unit 141 or a portion of the output unit 141 may be located elsewhere. For example, the output unit 141 may be located on a wall of an examination room in which the X-ray photographing of the object is performed.

The control units 113 and 150 control locations of the X-ray radiation unit 120 and the detector 130, photographing timing, and photographing conditions, according to photographing conditions set by the user.

In more detail, the control units 113 and 150 control the high voltage generator 121 and the detector 130 according to the command input via the input units 112 and 142 so as to control radiation timing of the X-ray, an intensity of the X-ray, and a region irradiated by the X-ray. In addition, the control units 113 and 150 adjust the location of the detector 130 according to a predetermined photographing condition, and controls operation timing of the detector 130.

Furthermore, the control units 113 and 150 generate a medical image of the object by using image data received via the detector 130. In detail, the control units 113 and 150 may receive the image data from the detector 130, and then, generate the medical image of the object by removing noise from the image data and adjusting a dynamic range and interleaving of the image data.

The output units 111 and 141 may output the medical image generated by the control units 113 and 150. The output units 111 and 141 may output information that is necessary for the user to manipulate the X-ray apparatus 100, for example, a user interface (UI), user information, or object information. Examples of the output unit may include a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

The workstation 110 shown in FIG. 1 may further include a communication unit (not shown) that may be connected to a server 162, a medical apparatus 164, and a portable terminal 166 via a network 1501.

The communication unit may be connected to the network 1501 by wire or wirelessly to communicate with the external server 162, the external medical apparatus 164, or the external portable terminal 166. The communication unit may transmit or receive data related to diagnosis of the object via the network 1501, and may also transmit or receive medical images captured by the medical apparatus 164, for example, a CT apparatus, an MRI apparatus, or an X-ray apparatus. Moreover, the communication unit may receive a medical history or treatment schedule of an object (e.g., a patient) from the server 162 to diagnose a disease of the object. Furthermore, the communication unit may perform data communication with the portable terminal 166 such as a mobile phone, a personal digital assistant (PDA), or a laptop computer of a medical doctor or a client, as well as the server 162 or the medical apparatus 164 in a hospital.

The communication unit may include one or more elements enabling communication with external apparatuses. For example, the communication unit may include a short distance communication module, a wired communication module, and a wireless communication module.

The short distance communication module refers to a module for performing short distance communication with an apparatus located within a predetermined distance. Examples of short distance communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (ND) conversion, high speed Fourier transformation, and an array process).

In addition, communication between the workstation 110 and the X-ray apparatus 100 may be performed using a high speed digital interface, such as low voltage differential signaling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

Figure 2:
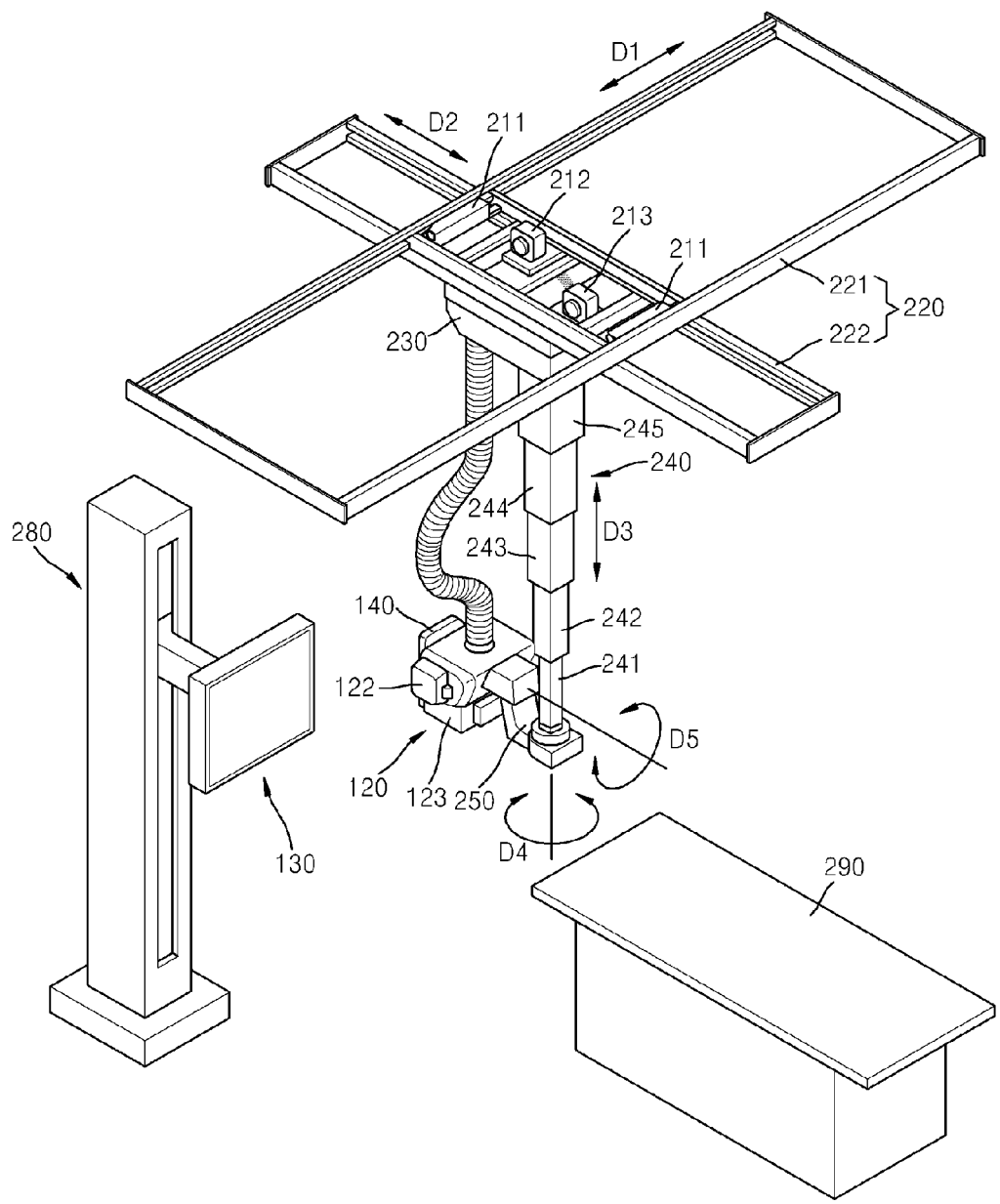
FIG. 2 is a perspective view of a fixed type X-ray apparatus.

FIG. 2 is a perspective view of a fixed type X-ray apparatus 200. The fixed type X-ray apparatus 200 may be another embodiment of the X-ray apparatus 100 of FIG. 1. Components included in the fixed type X-ray apparatus 200 that are the same as those of the X-ray apparatus 100 of FIG. 1 use the same reference numerals, and repeated descriptions thereof will be omitted.

Referring to FIG. 2, the fixed type X-ray apparatus 200 includes a manipulation unit 140 providing a user with an interface for manipulating the X-ray apparatus 200, an X-ray radiation unit 120 radiating an X-ray to an object, a detector 130 detecting an X-ray that has passed through the object, first, second, and third motors 211, 212, and 213 providing a driving power to transport the X-ray radiation unit 120, a guide rail 220, a moving carriage 230, and a post frame 240. The guide rail 220, the moving carriage 230, and the post frame 240 are formed to transport the X-ray radiation unit 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90°.

The first guide rail 221 is provided on the ceiling of an examination room in which the X-ray apparatus 200 is disposed.

The second guide rail 222 is located under the first guide rail 221, and is mounted so as to slide along the first guide rail 221. A roller (not shown) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 230 is disposed under the second guide rail 222 so as to move along the second guide rail 222. A roller (not shown) moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable, and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detector 130 detects the X-ray that has passed through the object, and may be combined with a table type receptor 290 or a stand type receptor 280.

A rotating joint 250 is disposed between the X-ray radiation unit 120 and the post frame 240. The rotating joint 250 allows the X-ray radiation unit 120 to be coupled to the post frame 240, and supports a load applied to the X-ray radiation unit 120.

The X-ray radiation unit 120 connected to the rotating joint 250 may rotate on a plane that is perpendicular to the third direction D3. In this case, a rotating direction of the X-ray radiation unit 120 may be defined as a fourth direction D4.

The X-ray radiation unit 120 may be configured to be rotatable on a plane perpendicular to the ceiling of the examination room. Therefore, the X-ray radiation unit 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray radiation unit 120 in the first, second, and third directions D1, D2, and D3. The first, second, and third motors 211, 212, and 213 may be electrically driven, and the first, second, and third motors 211, 212, and 213 may respectively include an encoder.

The first, second, and third motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 230. In another example, the first, second, and third motors 211, 212, and 213 may be connected to a power transfer unit (not shown) so as to linearly move the X-ray radiation unit 120 in the first, second, and third directions D1, D2, and D3. The driving power transfer unit may be a combination of a belt and a pulley, a combination of a chain and a sprocket, or a shaft, which are generally used.

In another example, motors (not shown) may be disposed between the rotating joint 250 and the post frame 240 and between the rotating joint 250 and the X-ray radiation unit 120 in order to rotate the X-ray radiation unit 120 in the fourth and fifth directions D4 and D5.

The manipulation unit 140 may be disposed on a side surface of the X-ray radiation unit 120.

Although FIG. 2 shows the fixed type X-ray apparatus 200 connected to the ceiling of the examination room, the fixed type X-ray apparatus 200 is merely an example for convenience of comprehension. That is, X-ray apparatuses according to embodiments of the present invention may include X-ray apparatuses having various structures that are well known to one of ordinary skill in the art, for example, a C-arm-type X-ray apparatus and an angiography X-ray apparatus, in addition to the fixed type X-ray apparatus 200 of FIG. 2.

Figure 3:
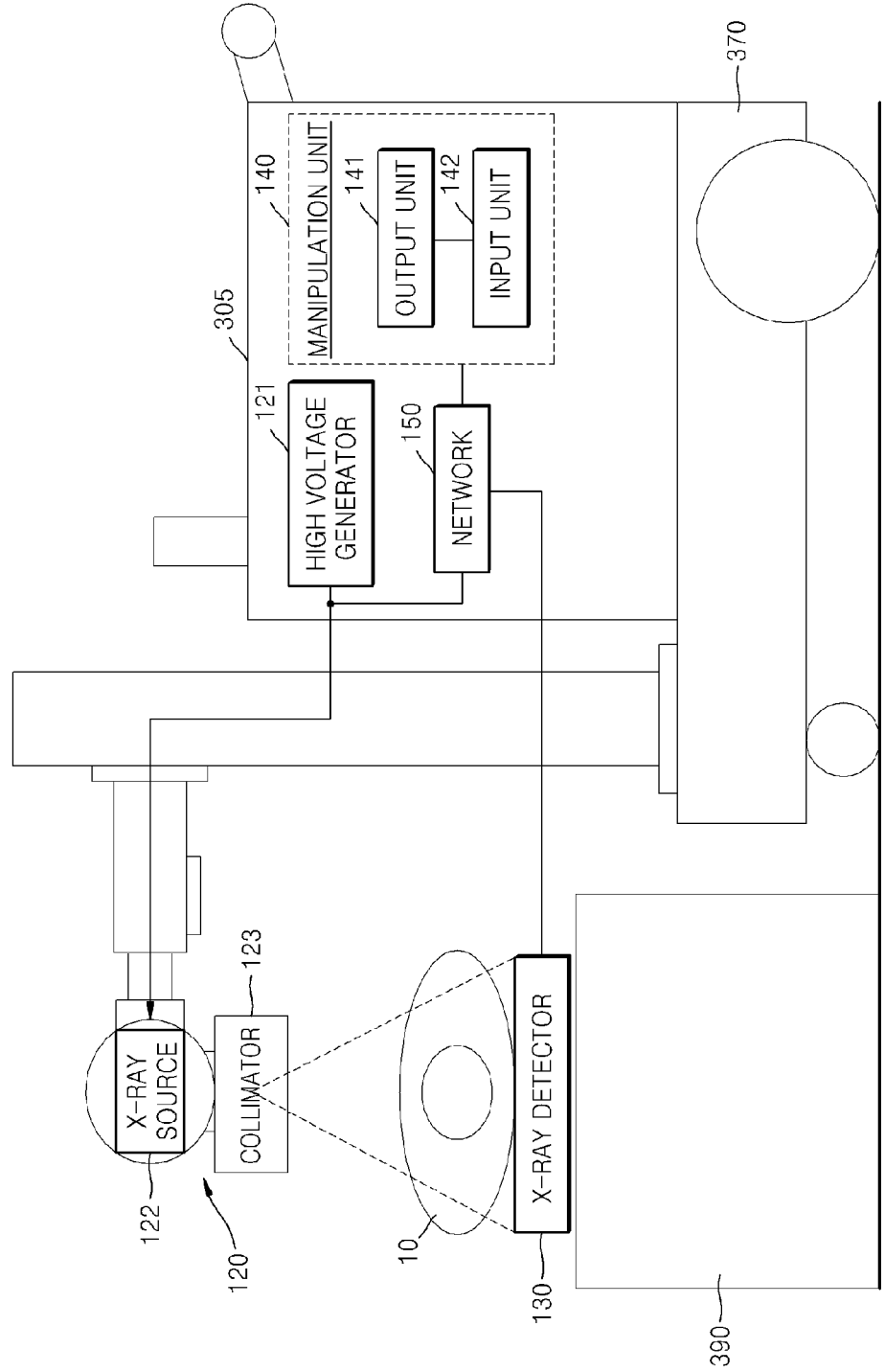
FIG. 3 is a diagram showing a configuration of a mobile X-ray apparatus capable of performing an X-ray photographing operation regardless of a place where the photographing operation is performed.

FIG. 3 is a diagram showing a configuration of a mobile X-ray apparatus 300 capable of performing an X-ray photographing operation regardless of a place where the photographing operation is performed. The mobile X-ray apparatus 300 may be another embodiment of the X-ray apparatus 100 of FIG. 1. Components included in the mobile X-ray apparatus 300 that are the same as those of the X-ray apparatus 100 of FIG. 1 use the same reference numerals as those used in FIG. 1, and a repeated description thereof will be omitted.

Referring to FIG. 3, the mobile X-ray apparatus 300 includes a transport unit 370 including a wheel for transporting the mobile X-ray apparatus 300, a main unit 305, an X-ray radiation unit 120, and a detector 130 detecting an X-ray that is radiated from the X-ray radiation unit 120 toward an object and transmitted through the object 10. The main unit 305 includes a manipulation unit 140 providing a user with an interface for manipulating the mobile X-ray apparatus 300, a high voltage generator 121 generating a high voltage applied to an X-ray source 122, and a control unit 150 controlling overall operations of the mobile X-ray apparatus 300. The X-ray radiation unit 120 includes the X-ray source 122 generating the X-ray, and a collimator 123 guiding a path along which the generated X-ray is emitted from the X-ray source 122 and adjusting an irradiation region radiated by the X-ray.

Although the detector 130 is combined with a table type receptor 390 in FIG. 3, the detector 130 may be combined with a stand type receptor.

In FIG. 3, the manipulation unit 140 is included in the main unit 305; however, embodiments of the present invention are not limited thereto. For example, the manipulation unit 140 of the mobile X-ray apparatus 300 may be disposed on a side surface of the X-ray radiation unit 120.

Figure 4:
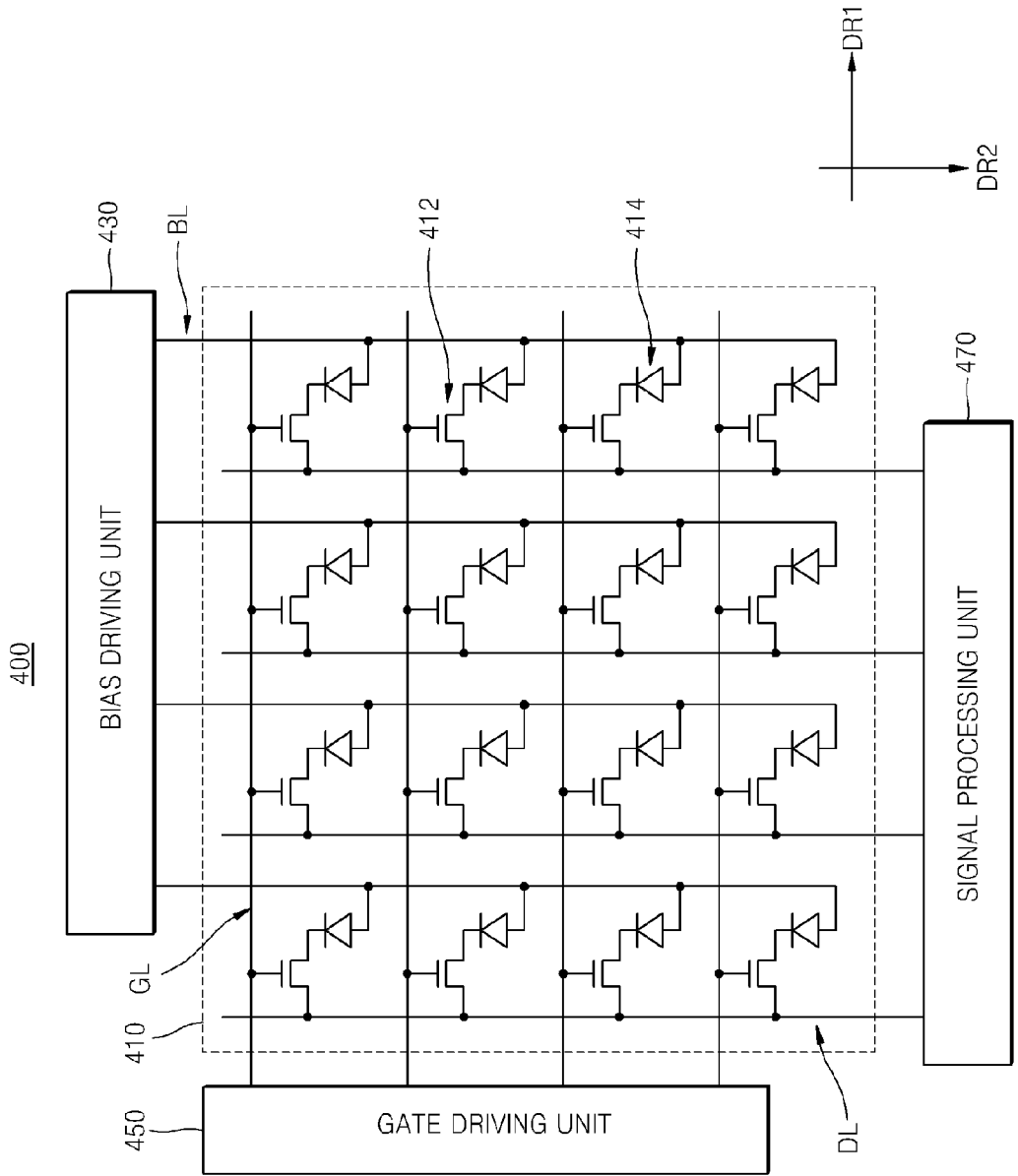
FIG. 4 is a diagram showing a detailed configuration of a detector.

FIG. 4 is a schematic diagram showing a detailed configuration of a detector 400. The detector 400 may be an embodiment of the detector 130 of FIGS. 1-3. The detector 400 may be an indirect type detector.

Referring to FIG. 4, the detector 400 may include a scintillator (not shown), a photodetecting substrate 410, a bias driving unit 430, a gate driving unit 450, and a signal processing unit 470.

The scintillator receives the X-ray radiated from the X-ray source 122 and converts the X-ray into light.

The photodetecting substrate 410 receives the light from the scintillator and converts the light into an electrical signal. The photodetecting substrate 410 may include gate lines GL, data lines DL, TFTs 412, photodiodes 414, and bias lines BL.

The gate lines GL may be formed in a first direction DR1, and the data lines DL may be formed in a second direction DR2 that crosses the first direction DR1. The first direction DR1 and the second direction DR2 may intersect perpendicularly to each other. FIG. 4 shows four gate lines GL and four data lines DL as an example.

The TFTs 412 may be arranged as a matrix in the first and second directions DR1 and DR2. Each of the TFTs 412 may be electrically connected to one of the gate lines GL and one of the data lines DL. A gate of the TFT 412 may be electrically connected to the gate line GL, and a source of the TFT 412 may be electrically connected to the data line DL. In FIG. 4, sixteen TFTs 412 (in a 4×4 arrangement) are shown as an example.

The photodiodes 414 may be arranged as a matrix in the first and second directions DR1 and DR2 so as to respectively correspond to the TFTs 412. Each of the photodiodes 414 may be electrically connected to one of the TFTs 412. An N-side electrode of each of the photodiodes 414 may be electrically connected to a drain of the TFT 412. FIG. 4 shows sixteen photodiodes 414 (in a 4×4 arrangement) as an example.

The bias lines BL are electrically connected to the photodiodes 414. Each of the bias lines BL may be electrically connected to P-side electrodes of an array of photodiodes 414. For example, the bias lines BL may be formed to be substantially parallel with the second direction DR2 so as to be electrically connected to the photodiodes 414. On the other hand, the bias lines BL may be formed to be substantially parallel with the first direction DR1 so as to be electrically connected to the photodiodes 414. FIG. 4 shows four bias lines BL formed along the second direction DR2 as an example.

The bias driving unit 430 is electrically connected to the bias lines BL so as to apply a driving voltage to the bias lines BL. The bias driving unit 430 may selectively apply a reverse bias voltage or a forward bias voltage to the photodiodes 414. A reference voltage may be applied to the N-side electrodes of the photodiodes 414. The reference voltage may be applied via the signal processing unit 470. The bias driving unit 430 may apply a voltage that is less than the reference voltage to the P-side electrodes of the photodiodes 414 so as to apply a reverse bias voltage to the photodiodes 414. On the other hand, the bias driving unit 430 may apply a voltage that is greater than the reference voltage to the P-side electrodes of the photodiodes 414 so as to apply a forward bias voltage to the photodiodes 414.

The gate driving unit 450 is electrically connected to the gate lines GL and thus may apply gate signals to the gate lines GL. For example, when the gate signals are applied to the gate lines GL, the TFTs 412 may be turned on by the gate signals. On the other hand, when the gate signals are not applied to the gate lines GL, the TFTs 412 may be turned off.

The signal processing unit 470 is electrically connected to the data lines DL. When the light received by the photodetecting substrate 410 is converted into the electrical signal, the electrical signal may be read out by the signal processing unit 470 via the data lines DL.

An operation of the detector 400 will now be described. During the operation of the detector 400, the bias driving unit 430 may apply the reverse bias voltage to the photodiodes 414.

While the TFTs 412 are turned off, each of the photodiodes 414 may receive the light from the scintillator and generate electron-hole pairs to accumulate electric charges. The number of electric charges accumulated in each of the photodiodes 414 may correspond to the number of X-rays.

Then, the gate driving unit 450 may sequentially apply the gate signals to the gate lines GL along the second direction DR2. When a gate signal is applied to a gate line GL and thus TFTs 412 connected to the gate line GL are turned on, photocurrents may flow into the signal processing unit 470 via the data lines DL due to the electric charges accumulated in the photodiodes 414 connected to the turned-on TFTs 412.

The signal processing unit 470 may convert the received photocurrents into image data and output the image data to the outside. The image data may be in the form of an analog signal or a digital signal corresponding to the photocurrents.

Although not shown in FIG. 4, if the detector 400 shown in FIG. 4 is a wireless detector, the detector 400 may further include a battery unit and a wireless communication interface unit. For example, the wireless communication interface unit may include a transmission unit and a reception unit according to an embodiment.

When compatibly using a plurality of X-ray detectors in one photographing space, although an operating environment of each of the X-ray detectors is not manually set by a user, if the operating environment of each X-ray detector is automatically set based on orientation information of an X-ray radiation unit and orientation information of an X-ray detector, a convenience of the user in a manipulation of an X-ray apparatus, especially, an operation of selecting or activating a desired X-ray detector to be used for photographing among the plurality of X-ray detectors, may increase. For example, orientation information of an X-ray radiation unit includes at least one of selected from position information of the X-ray radiation unit and directional information of the X-ray radiation unit and orientation information of an X-ray detector includes at least one of selected from position information of the X-ray detector and directional information of the X-ray detector.

When the user manually and directly selects an undesired X-ray detector from among the plurality of X-ray detectors to photograph an object, it is impossible to acquire an image of the object, and thus, the user again selects a desired X-ray detector to re-photograph the object. Due to the re-photographing, the user feels inconvenience, and an accumulation amount of radiation, to which the object is exposed, increases.

Therefore, according to an embodiment of the present invention, an X-ray detector is automatically selected or activated as an X-ray detector to be used for photographing, based on the orientation information of the X-ray radiation unit and the orientation information of the X-ray detector. Accordingly, the user easily photographs an object even without spending much time and effort in selecting the X-ray detector to be used for photographing.

Figure 5:
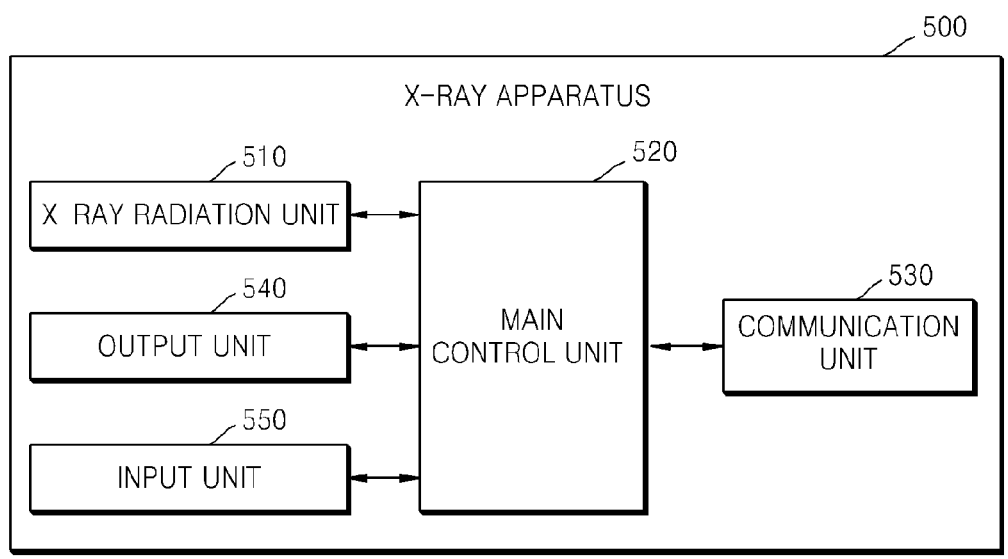
FIG. 5 is a block diagram of an X-ray apparatus according to an embodiment.

FIG. 5 is a block diagram of an X-ray apparatus 500 according to an embodiment.

The X-ray apparatus 500 may include an X-ray radiation unit 510, a main control unit 520, a communication unit 530, an output unit 540, and an input unit 550.

When the X-ray apparatus 500 of FIG. 5 is included in the X-ray system 1000 of FIG. 1, the X-ray apparatus 500 of FIG. 5 may correspond to the X-ray apparatus 100 of FIG. 1. In detail, the X-ray radiation unit 510, the main control unit 520, the output unit 540, and the input unit 550 of the X-ray apparatus 500 of FIG. 5 may respectively correspond to the X-ray radiation unit 120, the control unit 150, the output unit 141, and the input unit 142 of the X-ray apparatus 100 of FIG. 1. The communication unit 530 of the X-ray apparatus 500 of FIG. 5 may communicate with an X-ray detector by wires or wirelessly and may also communicate with an external apparatus via the network 1501 of FIG. 1. Thus, a repeated description thereof will be omitted.

The aforementioned components will now be described in detail.

The X-ray radiation unit 510 may generate X-rays and radiate the X-rays to an object.

The main control unit 520 may acquire orientation information of the X-ray radiation unit 510 and orientation information of an X-ray detector. For example, orientation information of the X-ray radiation unit 510 includes at least one of selected from position information of the X-ray radiation unit 510 and directional information of the X-ray radiation unit 510 and orientation information of an X-ray detector includes at least one of selected from position information of the X-ray detector and directional information of the X-ray detector.

For example, the position information of the X-ray radiation unit 510 may be a position vector of the X-ray radiation unit 510 in a global coordinate system that is expressed as an inertial frame in which an arbitrary location within an X-ray photographing space is the origin. This will be described in greater detail later with reference to FIG. 10.

Different pieces of position information of the X-ray radiation unit 510 may be acquired between when the X-ray apparatus 500 is the fixed type X-ray apparatus 200 and when the X-ray apparatus 500 is the mobile X-ray apparatus 300.

For example, in a global coordinate system that is expressed as an inertial frame in which an arbitrary location within an X-ray photographing space is the origin, when the X-ray apparatus 500 is the fixed type X-ray apparatus 200, the position information of the X-ray radiation unit 510 may be an absolute position vector of the X-ray radiation unit 510 acquired by using any of various sensors or apparatuses.

On the other hand, in a global coordinate system that is expressed as an inertial frame in which an arbitrary location within an X-ray photographing space is the origin, when the X-ray apparatus 500 is the mobile X-ray apparatus 300, the position information of the X-ray radiation unit 510 may be obtained by calculating a relative position vector of the X-ray radiation unit 510 based on an absolute position vector of the mobile X-ray apparatus acquired by using any of various sensors or apparatuses.

The directional information of the X-ray radiation unit 510 may also include information related to a directional orientation of the X-ray and information related to the X-ray irradiation region.

For example, the directional information of the X-ray radiation unit 510 may also be a normal vector of one surface of the X-ray radiation unit 510. Also, the directional information of the X-ray radiation unit 510 may also be a volume vector group corresponding to the X-ray irradiation region of the X-ray radiation unit 510 at various positions. This will be described in greater detail later with reference to FIGS. 12 and 15.

For example, the position information of the X-ray detector may be a position vector of the X-ray detector in a global coordinate system that is expressed as an inertial frame in which an arbitrary location within an X-ray photographing space is the origin. Also, the position information of the X-ray detector may be a volume vector group configured to include a plurality of position vectors existing within a predetermined distance from the position vector of the X-ray detector. This will be described in greater detail later with reference to FIGS. 9 and 16.

The directional information of the X-ray detector may also be a facing direction of the X-ray radiation unit 510. For example, the directional information of X-ray detector may also be a normal vector of one surface of the X-ray detector. In this case, a normal vector of an X-ray detector may be a direction perpendicular to a plane irradiated by an X-ray. The normal vector may also be a direction perpendicular to a plane formed by a photodetecting substrate 410.

This will be described in greater detail later with reference to FIG. 13.

In this case, the orientation information of the X-ray radiation unit 510 or the orientation information of the X-ray detector may be directly acquired by the main control unit 520 of the X-ray apparatus 500 by using any of various sensors or apparatuses.

For example, the orientation information of the X-ray radiation unit 510 or the orientation information of the X-ray detector may be acquired in real time by a camera or may be acquired using a wireless frequency.

In this case, since orientation information of an object within an X-ray photographing space may be acquired using any of various sensors or apparatuses according to various methods, such as methods of using light, electromagnetic waves, sound waves, a magnetic field, and an electric field, a method of acquiring the orientation information of the X-ray radiation unit 510 or the orientation information of the X-ray detector is not limited to a specific method.

The orientation information of the X-ray detector may also be acquired by using reference orientation information which are initial orientation information of the X-ray detector and using information related to orientation of the X-ray detector, that the communication unit 530 of the X-ray apparatus 500 has received from the X-ray detector. In this case, the main control unit 520 acquires the orientation information of the X-ray detector.

The reference orientation information includes at least one of selected from reference position information of the X-ray detector and reference directional information of the X-ray detector based on initial orientation of the X-ray detector.

For example, when an X-ray detector is coupled to a stand type receptor or a table type receptor, the reference position information of the X-ray detector may be position information corresponding to a location of the stand type receptor or the table type receptor.

Also, when an X-ray detector is coupled to a stand type receptor or a table type receptor, the reference directional information of the X-ray detector may be directional information corresponding to a directional of the stand type receptor or the table type receptor.

The reference orientation information is reset when the X-ray detector is coupled to a stand type receptor or a table type receptor.

In this connection, the X-ray apparatus 500 updates or resets the reference orientation information of the X-ray detector when the X-ray detector is coupled to a stand type receptor or a table type receptor, thereby minimizing the number of accumulated errors which occur in the calculation performed by the main control unit 520 to acquire the orientation information of the X-ray.

For example, information related to orientation of the X-ray detector may be information that is corresponding to a movement of the X-ray detector sensed by a sensor unit of the X-ray detector and is acquired based on the reference orientation information. This will be described in greater detail later with reference to FIG. 6.

In this case, the information related to orientation of the X-ray detector that is acquired in detector control unit of the X-ray detector may be transmitted via a communication unit 630 of the X-ray detector and may be received via the communication unit 530 of the X-ray apparatus 500.

The main control unit 520 may select the X-ray detector based on the orientation information of the X-ray radiation unit included therein and the orientation information of the X-ray detector. Also, the main control unit 520 may activate the X-ray detector based on the orientation information of the X-ray radiation unit included therein and the orientation information of the X-ray detector.

For example, the orientation information of the X-ray radiation unit 510 includes at least one of selected from the position information of the X-ray radiation unit 510 and the directional information of the X-ray radiation unit 510 and the orientation information of the X-ray detector includes at least one of selected from the position information of the X-ray detector and the directional information of the X-ray detector. In this case, the main control unit 520 may select the X-ray detector based on the position information of the X-ray radiation unit included therein and the position information of the X-ray detector. Also, the main control unit 520 may select the X-ray detector based on the directional information of the X-ray radiation unit included therein and the directional information of the X-ray detector. Also, the main control unit 520 may select the X-ray detector based on the directional information of the X-ray radiation unit included therein and the position information of the X-ray detector. Also, the main control unit 520 may select the X-ray detector based on the position information of the X-ray radiation unit included therein and the orientation information of the X-ray detector. This will be described in greater detail later with reference to FIGS. 11, 14, 17, 18 and 19.

The main control unit 520 may control the communication unit 530 to transmit to the X-ray detector a control signal generated in X-ray photographing sequence.

For example, the main signal includes at least one of selected from a signal for informing selection of the X-ray detector and a signal for activating the X-ray detector.

In this case, the signal for informing selection of the X-ray detector may be generated based on the orientation information of the X-ray radiation unit and the orientation information of the X-ray detector in the main control unit 520 of the X-ray apparatus. Also, the signal for activating the X-ray detector may be generated based on the orientation information of the X-ray radiation unit and the orientation information of the X-ray detector in the main control unit 520 of the X-ray apparatus.

Accordingly, the X-ray detector may be automatically activated based on the control signal.

For example, the control signal may be generated based on the position information of the X-ray radiation unit included therein and the position information of the X-ray detector. Also, the control signal may be generated based on the directional information of the X-ray radiation unit included therein and the directional information of the X-ray detector. Also, the control signal may be generated based on the directional information of the X-ray radiation unit included therein and the position information of the X-ray detector. Also, the control signal may be generated the X-ray detector based on the position information of the X-ray radiation unit included therein and the orientation information of the X-ray detector.

On the other hand, the signal for activating the X-ray detector may be generated based on a user's input.

For example, the X-ray detector and the X-ray apparatus may be connected to each other by wire or wirelessly, based on the signal for informing selection of the X-ray detector.

Furthermore, the X-ray detector is activated based on the user's input. For example, the X-ray detector may be activated in response to a radiation-prepare signal input via the radiation switch or a special input according to the user's input conducted before the radiation-prepare signal is received.

The main control unit 520 may also control an operation of the X-ray radiation unit 510, based on identification information of the selected X-ray detector.

For example, the identification information of the X-ray detector may include type information and size information of the X-ray detector.

For example, types of X-ray detectors may be categorized into X-ray detectors using a direct detection method, which detects X-rays by reading out an electron-hole pair that is generated through a direct reaction with the X-rays, and X-ray detectors using an indirect detection method that detects and reads out light into which X-rays are converted via a scintillator.

For example, when not an X-ray detector having a size of 14 inch×17 inch but an X-ray detector having a size of 17 inch×17 inch is selected, at least one of an X-ray radiation direction and an X-ray irradiation region of the X-ray radiation unit 510 may be adjusted in correspondence with the size of the selected X-ray detector. Moreover, the X-ray source of the X-ray radiation unit 510 may rotate and move in a front direction, a rear direction, a left direction, a right direction, an up direction, or a down direction or at a certain angle in order for the X-ray radiation unit 510 to radiate an X-ray having the same size as the size of the selected X-ray detector. In addition, a size of a collimator included in the X-ray radiation unit 510 may be automatically adjusted in order for the X-ray radiation unit 510 to radiate an X-ray having the same size as the size of the selected X-ray detector. In other words, when the X-ray detector having the size of 17 inch×17 inch is selected, the size of the collimator may be automatically adjusted such that an area of X-rays reaching the X-ray detector is equal to the size of 17 inch×17 inch, and when the X-ray detector having the size of 14 inch×17 inch is selected, the size of the collimator may be automatically adjusted such that an area of X-rays reaching the X-ray detector is equal to the size of 14 inch×17 inch.

Furthermore, the main control unit 520 may automatically control an orientation of the X-ray radiation unit 510, based on the orientation information of the selected X-ray detector For example, a main control unit of an X-ray apparatus according to an embodiment may control orientation of an X-ray radiation unit so that the X-ray radiation unit and a selected X-ray detector may face each other, based on orientation information of the selected X-ray detector.

In this case, the position of the X-ray radiation unit may be controlled based on the position information of the selected X-ray detector, and the direction of the X-ray radiation unit may be controlled based on the direction information of the selected X-ray detector. The direction of the X-ray radiation unit may be controlled based on the position information of the selected X-ray detector, and the position of the X-ray radiation unit may be controlled based on the direction information of the selected X-ray detector. The position and direction of the X-ray radiation unit may be simultaneously or sequentially controlled based on the position information and direction information of the selected X-ray detector.

This will be described in more detail later with reference to FIG. 22.

The main control unit 520 of the X-ray apparatus 500 according to an embodiment may determine whether the X-ray radiation unit 510 and the X-ray detector 600 face each other, based on orientation information of the X-ray radiation unit 510 and orientation information of the X-ray detector 600.

For example, the orientation information of the X-ray radiation unit 510 or the orientation information of the X-ray detector 600 may be directly acquired by the main control unit 520 of the X-ray apparatus 500 by using any of various sensors or apparatuses.

The orientation information of the X-ray detector may be acquired by the detector control unit included in the X-ray detector, based on the orientation of the X-ray detector sensed by the sensor unit included in the X-ray detector.

For example, the orientation information of the X-ray radiation unit may include at least one selected from the position information of the X-ray radiation unit and the direction information thereof, and the orientation information of the X-ray detector may include at least one selected from the position information of the X-ray detector and the direction information thereof.

When the X-ray radiation unit 510 is adjacent to the X-ray detector 600, the main control unit 520 of the X-ray apparatus 500 may determine that the X-ray radiation unit 510 and the X-ray detector 600 face each other. For example, when a difference between distances indicated by the position information of the X-ray radiation unit 510 and the position information of the X-ray detector 600 is within a predetermined range, the main control unit 520 may determine that the X-ray radiation unit 510 and the X-ray detector 600 face each other. This will be described in greater detail later with reference to FIG. 11.

When the direction in which the X-ray radiation unit 510 radiates an X-ray is opposite to the direction in which the X-ray detector 600 is oriented, the main control unit 520 of the X-ray apparatus 500 may determine that the X-ray radiation unit 510 and the X-ray detector 600 face each other. For example, when a difference between angles indicated by the direction information of the X-ray radiation unit 510, indicating the radiation direction of an X-ray, and the direction information of the X-ray detector 600, indicating the direction in which the X-ray detector 600 faces the X-ray radiation unit 510, is within a predetermined range, the main control unit 520 may determine that the X-ray radiation unit 510 and the X-ray detector 600 face each other. This will be described in greater detail later with reference to FIG. 14.

When a region irradiated by the X-ray radiated by the X-ray radiation unit 510 is adjacent to the position of the X-ray detector 600, the main control unit 520 of the X-ray apparatus 500 may determine that the X-ray radiation unit 510 and the X-ray detector 600 face each other. For example, when the position information of the X-ray detector 600 is included in the direction information of the X-ray radiation unit 510, representing the region irradiated by the X-ray, the main control unit 520 may determine that the X-ray radiation unit 510 and the X-ray detector 600 face each other. This will be described in greater detail later with reference to FIGS. 17-19.

When the main control unit 520 determines that the X-ray radiation unit 510 and the X-ray detector 600 face each other, the main control unit 520 may select an X-ray detector. When the main control unit 520 determines that the X-ray radiation unit 510 and the X-ray detector 600 face each other, the main control unit 520 may activate an X-ray detector.

On the other hand, when the X-ray radiation unit 510 and the X-ray detector 600 do not face each other, the main control unit 520 of the X-ray apparatus 500 may control orientation of the X-ray radiation unit 510 so that the X-ray radiation unit 510 and the X-ray detector 600 may face each other, based on the orientation information of the X-ray detector 600.

The main control unit 520 may also control information about whether the X-ray radiation unit 510 and the X-ray detector 600 face each other so that the information may be output via the output unit of the X-ray apparatus or the output unit of the X-ray detector.

For example, the output unit 640 of the X-ray detector 600 may include an LCD, an LED, a light-emitting device, and the like, and, when the X-ray radiation unit 510 and the X-ray detector 600 do not face each other, the output unit 640 may flicker to instruct a user to change orientation of the X-ray detector 600 or the X-ray radiation unit 510. Accordingly, when a user tries to perform X-ray photographing on an object, photographing errors may be reduced and thus the amount of exposure of the object to radiation during X-ray photographing may be reduced. In addition, more accurate X-ray images may be obtained.

The output unit 640 of the X-ray detector 600 may include an LCD, an LED, a light-emitting device, and the like, and, when the X-ray radiation unit 510 and the X-ray detector 600 face each other, the output unit 640 may flicker to inform a user that the X-ray detector 600 is ready for X-ray photographing. Also, the output unit 640 may flicker as sound to inform a user that the X-ray detector 600 is ready for X-ray photographing.

Also, the output unit 640 may be displayed to inform a user that the X-ray detector 600 is selected for X-ray photographing.

The communication unit 530 of the X-ray apparatus 500 includes a transmission unit and receive unit and may be connected to the network by wire or wirelessly to communicate with the X-ray detector or the workstation.

For example, when the X-ray detector is selected by the main control unit, the communication unit 530 of the X-ray apparatus 500 may be connected to the network by wire or wirelessly to communicate with the selected X-ray detector. In other word, the X-ray apparatus and the X-ray detector may be connected to each other by wire or wirelessly. When they are connected to each other wirelessly, a device (not shown) for synchronizing clock signals with each other may be further included.

In this case, the X-ray detector and the X-ray apparatus transmit or receive signals to be generated during X-ray photographing operation each other via network.

For example, the main control unit 520 may transmit a prepare signal to the X-ray detector so that the X-ray detector may prepare to detect the X-ray transmitted through the object. The X-ray detector prepares to detect the X-ray in response to the prepare signal, and when the preparing for the detection is finished, the X-ray detector transmits a ready signal to the main control unit 520.

Also, when the high voltage generator 121 receives the prepare signal from the main control unit 520, the high voltage generator 121 may transmit a prepare signal to the X-ray detector so that the X-ray detector may prepare to detect the X-ray transmitted through the object.

And then, the X-ray detector prepares to detect the X-ray in response to the prepare signal, and when the preparing for the detection is finished, the X-ray detector transmits a ready signal to the high voltage generator 121. In this case, the high voltage generator 121 transmit the ready signal to the main control unit 520.

Also, the X-ray apparatus may transmit a signal for informing selection of the X-ray detector, the X-ray detector may be activated based on the signal received from the X-ray apparatus. In this case, the X-ray detector may prepare to receive X-ray irradiation during X-ray photographing.

The communication unit 530 may transmit a signal for activating the X-ray detector to the X-ray detector to be used for photographing.

Also, the communication unit 530 may receive information related to the orientation of the X-ray detector from the X-ray detector.

For example, the information related to the orientation of the X-ray detector may be information that is related with a movement of the X-ray detector 600 sensed by the sensor unit 610 of the X-ray detector 600 and is acquired based on the initial orientation information of the X-ray detector 600 In this case, the information related to the orientation of the X-ray detector may be acquired in the main control unit 520.

In addition, a user may register at least one X-ray detector in a main control unit of an X-ray apparatus in advance before X-ray photographing is performed, and thus the main control unit may acquire ID information and IP information of the X-ray detector in advance. Accordingly, the X-ray apparatus may communicate with the X-ray detector via a wired or wireless network.

In this case, the main control unit receives information related with orientation information including at least one selected from position information and direction information from the at least one X-ray detector via the communication unit 630, and then transmits a control signal to a selected X-ray detector via the communication unit 630. Alternatively, when the X-ray detector transmits the orientation information to the main control unit, the X-ray detector may also transmit the ID information of the X-ray detector.

The X-ray apparatus 500 may further include the output unit 540 and the input unit 550.

The output unit 540 may display information about a plurality of X-ray detectors selectable by a user.

Alternatively, the output unit 540 may output pieces of information about only a plurality of X-ray detectors located in a predetermined direction from the X-ray radiation unit 510.

In this case, the pieces of information about the X-ray detectors may be arranged according to a predetermined arrangement criterion and then output.

The input unit 550 may receive a selection signal for selecting at least one X-ray detector from among the plurality of X-ray detectors displayed on the output unit 540.

This will be described in greater detail later with reference to FIG. 20.

The input unit 550 may be a touch pad. In detail, the input unit 550 may include a touch pad (not shown) coupled with a display panel (not shown) included in the output unit 540. The output unit 540 displays a user interface (UI) image on the display panel. When a user inputs a command by touching a certain point on the UI image, the touch pad may sense the input operation and recognize the command input by the user.

In detail, when the input unit 550 is a touch pad and the user touches a certain point on the UI image, the input unit 550 senses the touched point. Then, the input unit 550 may transmit sensed information to the main control unit 520. Thereafter, the main control unit 520 may recognize a user's request or command corresponding to the sensed information and may perform the recognized user's request or command.

Figure 6:
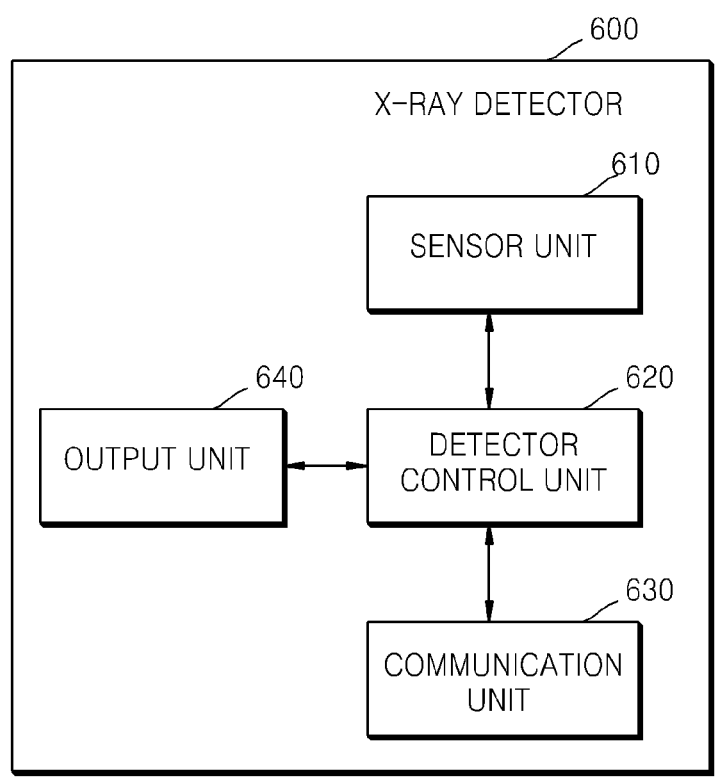
FIG. 6 is a block diagram of an X-ray detector according to an embodiment.

FIG. 6 is a block diagram of an X-ray detector 600 according to an embodiment.

The X-ray detector 600 may include a sensor unit 610, a detector control unit 620 and a communication unit 630. The X-ray detector 600 may further include an output unit 640. The X-ray detector 600 may be at least one selected from a wired X-ray detector and a wireless X-ray detector.

When the X-ray detector 600 is included in the X-ray system 1000 of FIG. 1, the X-ray detector 600 may correspond to the detector 130 of FIG. 1. As described above, the X-ray detector 600 may be separated from the X-ray apparatus 100 of FIG. 1. Thus, a repeated description thereof will be omitted.

The aforementioned components will now be described in detail.

The sensor unit 610 may sense orientation of the X-ray detector 600.

For example, the sensor unit 610 may sense a movement of the X-ray detector 600 based on the initial orientation information of the X-ray detector 600.

For example, the sensing unit 610 may be a gyroscope sensor, a geomagnetic sensor, an inertial measurement unit (IMU), an accelerometer, a magnetometer, and GPS sensor, or the like.

In this case, since the movement of the X-ray detector 600 may be sensed using any of various sensors according to any of various methods that are widely used in the art, a method of sensing the movement of the X-ray detector 600 is not limited to a specific method.

The detector control unit 620 may acquire the orientation information of the X-ray detector 600 based on the orientation of the X-ray detector 600 sensed in the sense unit 610.

For example, the orientation information of the X-ray detector 600 includes at least one of selected from position information of the X-ray detector and directional information of the X-ray detector.

Also, the detector control unit 620 of the X-ray detector 600 may acquire orientation information of the X-ray detector 600 by using the reference orientation information which is the initial orientation information of the X-ray detector 600 and the information related to the orientation of the X-ray detector 600 according to the movement of the X-ray detector 600 sensed in the sense unit 610. In this case, the information related to orientation of the X-ray detector 600 according to the movement of the X-ray detector 600 may be acquired in the detector control unit 620.

For example, the information related to the orientation of the X-ray detector 600 according to the movement of the X-ray detector 600 includes at least one of selected from the information related to the position of the X-ray detector 600 and the information related to the directional of the X-ray detector 600.

Also, the information related to the orientation of the X-ray detector 600 according to the movement of the X-ray detector 600, may be information indicating at least one of selected from a moving direction, a moving angle and a moving distance of the X-ray detector 600 which have been detected by the sensing unit 610 based on the reference orientation information which is the initial orientation information of the X-ray detector 600.

In this case, the information related to the orientation of the X-ray detector 600 according to the movement of the X-ray detector 600 may be information indicating at least one of selected from a moving direction, a moving angle and a moving distance of the X-ray detector 600 which have been detected by the sensing unit 610 at certain time intervals. The certain time interval may include a time interval such as one second, ten seconds, or one minute.

In this case, since the information of related to the orientation of the X-ray detector 600 according to a movement of the X-ray detector 600 may be sensed using any of various sensors according to any of various methods that are widely used in the art, a method of sensing information of related to the orientation of the X-ray detector 600 according to a movement of the X-ray detector 600 is not limited to a specific method.

The communication unit 630 includes a transmission unit and a reception unit.

The communication unit 630 may transmit the orientation information of the X-ray detector to the X-ray apparatus via a wireless network.

For example, the orientation information of the X-ray detector 600 includes at least one of selected from position information of the X-ray detector and directional information of the X-ray detector.

The communication unit 630 may receive the control signal from the X-ray apparatus.

For example, the control signal received from the X-ray apparatus may be a signal for activating the X-ray detector 600.

In this case, the detector control unit 620 may control the X-ray detector 600 to be activated, according to the control signal received by the communication unit 630.

On the other hand, the control signal received from the X-ray apparatus may also be a signal of informing selection of the X-ray detector indicating whether the X-ray detector 600 has been selected in the main control unit of the X-ray apparatus.

Also, when the X-ray detector is activated, the X-ray detector may prepare to acquire an X-ray image to object. For example, the X-ray detector may prepare to reset a photo detection unit or to receive irradiated X-ray from the X-ray radiation unit.

For example, when the X-ray detector is in a sleep mode, the X-ray detector is changed into a normal mode when receiving a notification signal from the control unit. At this time, the X-ray detector normalizes a clock signal of the control unit, and a photodetection unit of the X-ray detector may perform a reset operation (flushing) at faster intervals than in the sleep mode.

As another example, soon after previous X-ray photographing is performed, the X-ray detector maintains a normal mode. In this case, a reset cycle of the photodetection unit may be adjusted in accordance with a current X-ray photographing stage. Other operations for preparing for X-ray photographing may be performed.

Thereafter, in response to a prepare signal input via an input unit, that is, a radiation switch, the X-ray detector completes preparation for X-ray detection. Then, when an X-ray is radiated to the X-ray detector according to a radiation command input via the X-ray radiation switch, the X-ray detector receives a radiated X-ray and generates X-ray image data of an object. Next, the X-ray detector transmits the image data to the control unit via the communication path. As described above, the activation of the detector may be automatically performed based on the notification from the control unit.

As another example, the X-ray detector may be connected to the X-ray apparatus via a wireless network based on the signal for informing selection of the X-ray detector from the X-ray apparatus. In this case, the X-ray detector may be activated based on the user's input through input unit.

For example, the activation of the detector may not be performed until special signal inputs via the input units 112 and 142 are received. For example, the detector may be activated in response to a radiation-prepare signal input via the radiation switch or a special input conducted before the radiation-prepare signal is received.

As described above, the X-ray detector 600 may further include the output unit 640. The detector control unit 620 may control the output unit 640 to display the information indicating whether the X-ray detector 600 has been selected or/and activated, according to the control signal received by the communication unit 630.

Examples of the output unit 640 of the X-ray detector 600 may include an LCD, an LED, and a light-emitting device (for example, flicking when the X-ray detector 600 is activated) which are for outputting the information indicating whether the X-ray detector 600 has been selected or/and activated.

Also, when the X-ray detector receives the signal for informing selection of the X-ray detector, the detector control unit may transmit a sound output signal to the output unit 640 so that the output unit 640 output a predetermined sound and the object or the user may recognize whether the X-ray detector 600 has been selected to be used for photographing.

Also, when the X-ray detector receives the signal for activating the X-ray detector, the detector control unit may transmit a sound output signal to the output unit 640 so that the output unit 640 output a predetermined sound and the object or the user may recognize whether the X-ray detector 600 has been activated.

Figure 7:
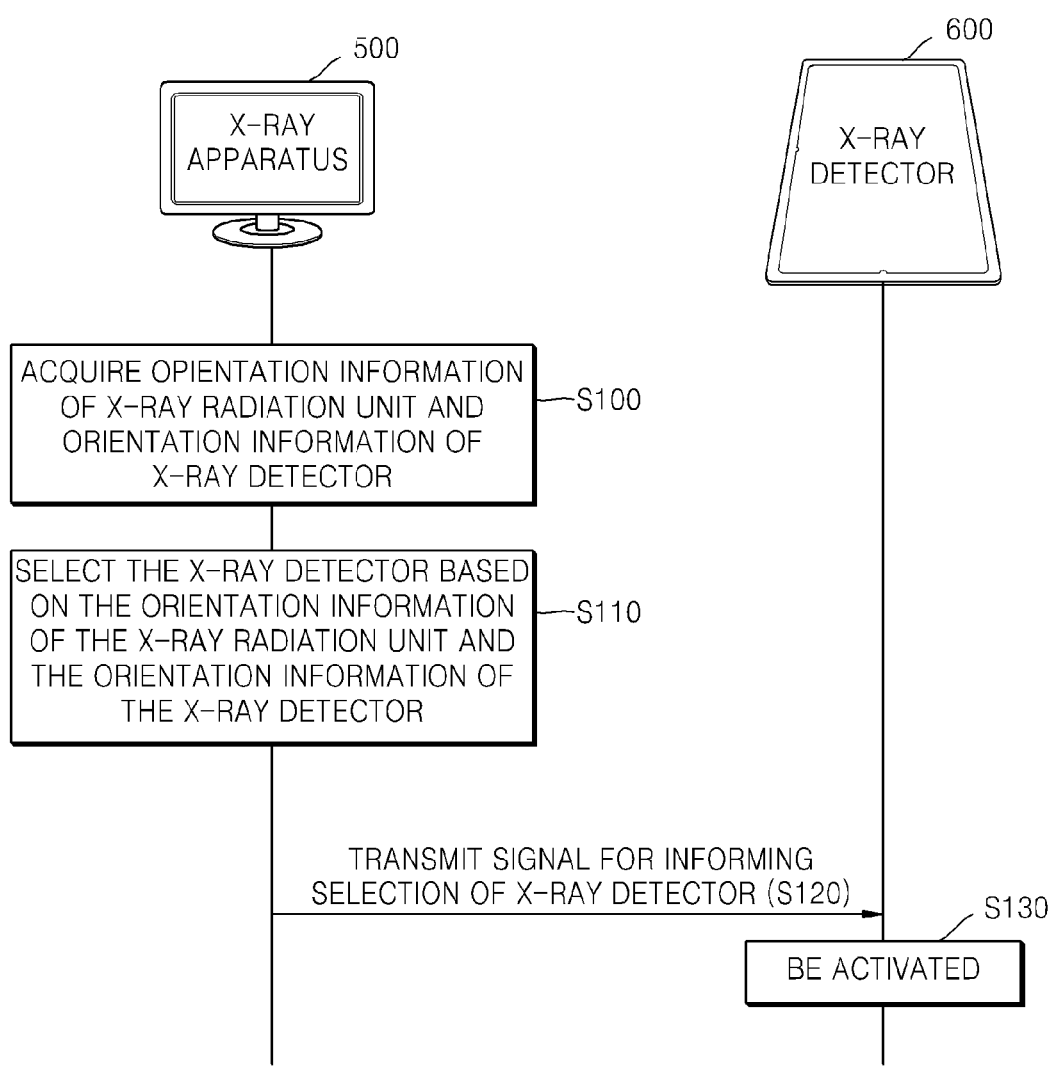
FIG. 7 is a diagram for describing respective operations of an X-ray apparatus and an X-ray detectors according to an embodiment.

FIG. 7 is a diagram for describing respective operations of the X-ray apparatus 500 and the X-ray detector 600 according to an embodiment.

In operation S100, the X-ray apparatus 500 acquires orientation information of the X-ray radiation unit 510 and orientation information of the X-ray detector by using any of various sensors or apparatuses.

For example, the X-ray apparatus 500 directly acquires orientation information of the X-ray radiation unit 510 and orientation information of the X-ray detector by using any of various sensors or apparatuses.

On the other hand, the orientation information of the X-ray detector may also be acquired by using reference orientation information which is initial orientation information of the X-ray detector and using information related to orientation of the X-ray detector, that the communication unit 530 of the X-ray apparatus 500 has received from the X-ray detector. In this case, the main control unit 520 acquires the orientation information of the X-ray detector.

For example, orientation information of the X-ray radiation unit 510 includes at least one of selected from position information of the X-ray radiation unit 510 and directional information of the X-ray radiation unit 510 and orientation information of an X-ray detector includes at least one of selected from position information of the X-ray detector and directional information of the X-ray detector.

In operation S110, the X-ray apparatus 500 selects the X-ray detector 600 based on the orientation information of the X-ray radiation unit and the orientation information of the X-ray detector acquired in operation S100.

On the other hand, the X-ray apparatus 500 generates a signal for activating the X-ray detector 600 based on the orientation information of the X-ray radiation unit and the orientation information of the X-ray detector acquired in operation S100.

In operation S120, the X-ray apparatus 500 transmits the signal for informing selection of the X-ray detector indicating whether the X-ray detector 600 has been selected in the main control unit of the X-ray apparatus.

On the other hand, the X-ray apparatus 500 transmits the signal of activating the X-ray detector selected in operation S110.

In operation S130, the X-ray detector 600 is activated based on the signal (i.e., the control signal) received by the X-ray apparatus 500.

Figure 8:
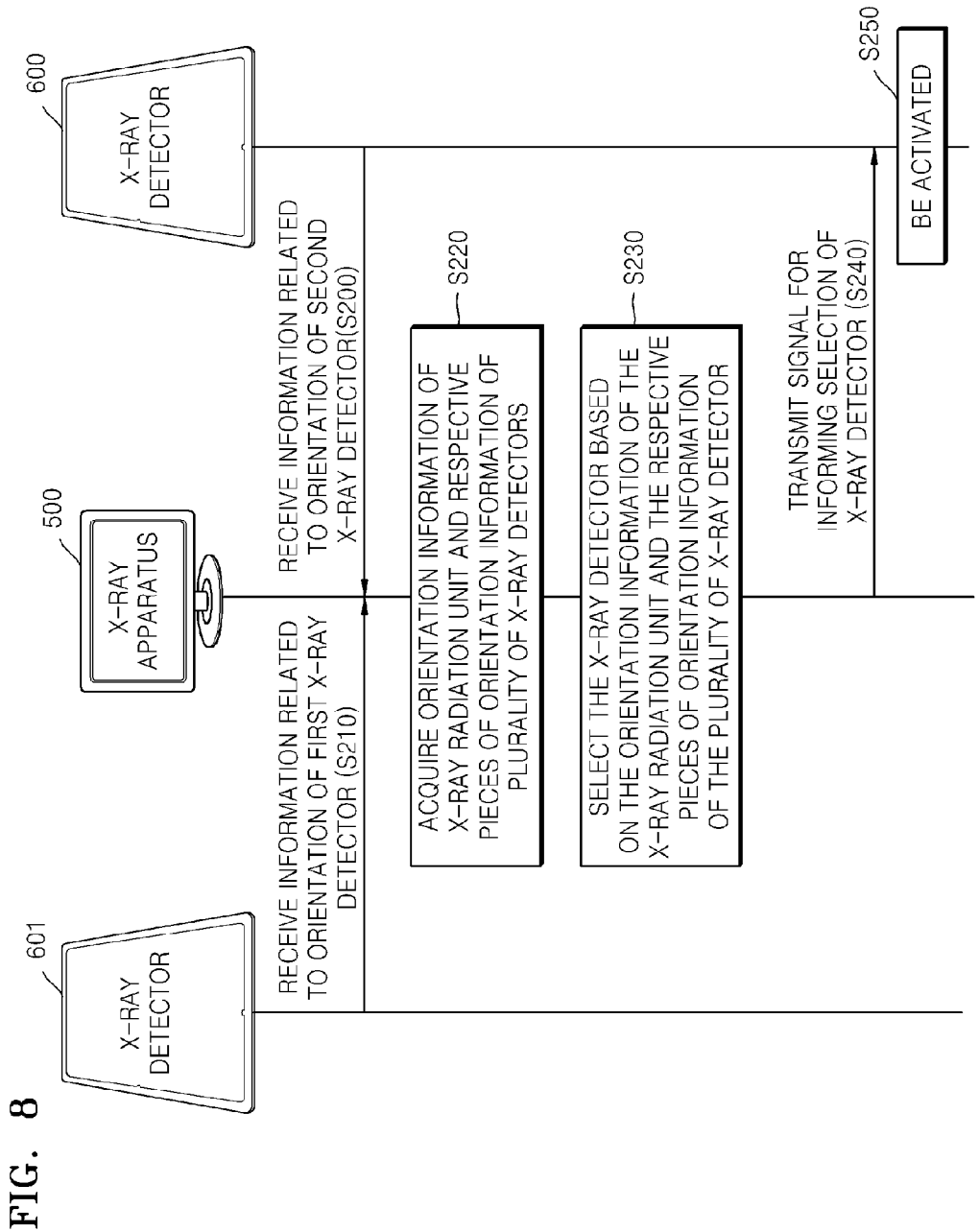
FIG. 8 is a diagram for describing respective operations of an X-ray apparatus and a plurality of X-ray detectors according to an embodiment.

FIG. 8 is a diagram for describing respective operations of the X-ray apparatus 500 and X-ray detectors 600 and 601 according to another embodiment.

In operations S200 and S210, the X-ray apparatus 500 receives pieces of information related to the orientation of the X-ray detectors 600 and 601 from the X-ray detectors 600 and 601, respectively.

For example, the pieces of information related to the orientation of the X-ray detectors 600 and 601 may be acquired in relation to movements of the X-ray detectors 600 and 601 sensed by respective sensor units of the X-ray detectors 600 and 601, based on respective pieces of initial orientation information of the X-ray detectors 600 and 601. In this case, the detector control unit of the X-ray detectors 600 and 601 directly acquired information related to the orientation of the X-ray detectors 600 and 601. For example, the orientation information of an X-ray detector includes at least one of selected from position information of the X-ray detector and directional information of the X-ray detector.

In operation S220, the X-ray apparatus 500 acquires orientation information of the X-ray radiation unit 510 and respective pieces of orientation information of a plurality of X-ray detectors 600 and 601.

For example, the orientation information of the X-ray detector may also be acquired by using reference orientation information which is initial orientation information of the X-ray detector and using information related to orientation of the X-ray detectors in operation S200 and S210 that the communication unit 530 of the X-ray apparatus 500 has received from the X-ray detectors.

In this case, the reference orientation information includes at least one of selected from reference position information of the X-ray detector and reference directional information of the X-ray detector based on initial orientation of the X-ray detector.

Operations S230, S240, and S250 of the X-ray detectors 600 and 601 correspond to operations S110-S130 of a single X-ray detector 600 of FIG. 7, respectively, and thus detailed descriptions thereof will be omitted.

Figure 9:
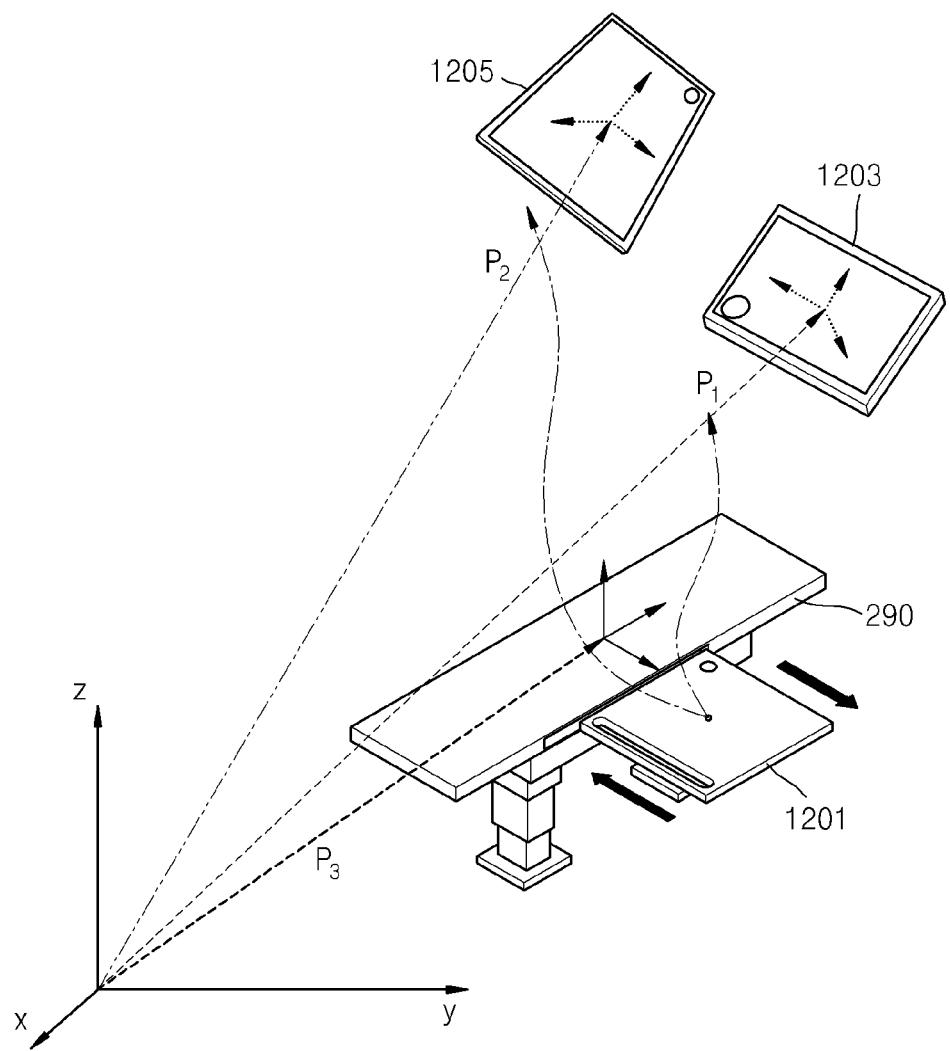
FIG. 9 illustrates an example in which the X-ray apparatus of FIG. 5 acquires position information of an X-ray detector.

FIG. 9 illustrates an example in which the X-ray apparatus of FIG. 5 acquires position information of an X-ray detector.

As illustrated in FIG. 9, the X-ray detectors 1201, 1203, and 1205 may be freely dispersed within a single X-ray photographing space, the X-ray apparatus 500 acquires respective position information of X-ray detectors 1201, 1203, and 1205.

The X-ray detectors 1201, 1203, and 1205 may be inserted into a stand type receptor (not shown) or a table type receptor 290 of the X-ray apparatus 500 and thus may be used as fixed type X-ray detectors. Alternatively, the X-ray detectors 1201, 1203, and 1205 may be separated from the table type receptor 290 of the X-ray apparatus 500 and thus may be used as mobile X-ray detectors.

The X-ray detectors 1201, 1203, and 1205 may be movable to various locations within the X-ray photographing space. For example, as illustrated in FIG. 9, the X-ray detector 1201 having been coupled with the table type receptor 290 may be illustrated as the X-ray detector 1203 or 1205 that may exist at various locations, as the X-ray detector 1201 moves within the X-ray photographing space.

As illustrated in FIG. 9, respective pieces of position information of the X-ray detectors 1201, 1203, and 1205 may be position vectors of the respective the X-ray detectors 1201, 1203, and 1205 in a global coordinate system that is expressed as an inertial frame in which an arbitrary location within an X-ray photographing space is the origin.

For example, a position vector $P_1$ of the center of the X-ray detector 1203 and a position vector $P_2$ of the center of the X-ray detector 1205 may be acquired as the respective pieces of position information of the X-ray detectors 1203 and 1205.

The position vector $P_1$ and the position vector $P_2$ may be directly acquired by the X-ray apparatus 500 by using any of various sensors or apparatuses.

In this case, since position information of an object within an X-ray photographing space may be acquired using any of various sensors or apparatuses according to any of various methods, such as methods of using light, electromagnetic waves, sound waves, a magnetic field, and an electric field, a method of acquiring the respective position vectors of the X-ray detectors 1201, 1203, and 1205 is not limited to a specific method.

The position vector $P_1$ and the position vector $P_2$ may be acquired by using pieces of reference position information which are respective pieces of initial position information of the X-ray detectors 1203 and 1205 and using respective pieces of information related to orientation of the X-ray detectors 1203 and 1205 received from the X-ray detectors 1203 and 1205.

For example, when the X-ray detectors 1201, 1203, and 1205 are coupled to the stand type receptor (not shown) or the table type receptor 290, respective pieces of reference position information of the X-ray detectors 1201, 1203, and 1205 may be position information corresponding to a location of the stand type receptor (not shown) or the table type receptor 290.

As illustrated in FIG. 9, the respective pieces of reference position information of the X-ray detectors 1201, 1203, and 1205 may be a position vector $P_3$ of the table type receptor 290 in a global coordinate system that is expressed as an inertial frame in which an arbitrary location within an X-ray photographing space is the origin.

For example, the position information of the stand type receptor (not shown) or the table type receptor 290 in relation to one point of the X-ray photographing space (for example, a distal end of one corner of a bottom of the X-ray photographing space, a distal end of one corner of a ceiling of the X-ray photographing space, and a central point of the X-ray photographing space) may be predetermined. For example, the position information of the table type receptor 290 in relation to the distal end of one corner of the bottom of the X-ray photographing space may be determined as a coordinate value of (2, 2, 1). Alternatively, a coordinate value representing a position of the stand type receptor or the table type receptor 290 may be predetermined as the origin. For example, current position information of the table type receptor 290 within the X-ray photographing space may be predetermined as a coordinate value of (0, 0, 0).

In more detail, the X-ray detectors 1201, 1203, and 1205 may be inserted into the table type receptor 290 and thus the X-ray detector 1201 may be connected to the table type receptor 290. For example, a position of a magnet included in the table type receptor 290 may be detected by respective sensors (for example, a magnetometer) included in the X-ray detectors 1201, 1203, and 1205, and thus, whether the X-ray detectors 1201, 1203, and 1205 are connected to the table type receptor 290 may be determined.

When the X-ray detector 1201 is inserted into the table type receptor 290, the X-ray detector 1201 may be identified as a fixed-type X-ray detector. When the respective sensors of the X-ray detectors 1203 and 1205 are separated from the magnet included in the table type receptor 290, the X-ray detectors 1203 and 1205 may be identified as movable X-ray detectors.

By inserting the X-ray detectors 1201, 1203, and 1205 into the table type receptor 290, position information (for example, (1, 1, 0.5)) of the table type receptor 290 may be determined as the reference position information of each of the X-ray detectors 1201, 1203, and 1205.

For example, the detector control unit may acquire the information related to orientation of the X-ray detector based on the orientation of the X-ray detector sensing by the sensing unit. On the other hand, a sensor control unit (not shown) may acquire the information related to orientation of the X-ray detector based on the orientation of the X-ray detector sensed by the sensing unit.

For example, the information related to orientation of the X-ray detector related to the information related to the position of the X-ray detector, the respective pieces of position variation information of the X-ray detectors 1203 and 1205 may be pieces of information that are related with movements of the X-ray detectors 1203 and 1205 sensed by the respective sensor units of the X-ray detectors 1203 and 1205 and are acquired based on the position information of the table type receptor 290, namely, the initial position information of each of the X-ray detectors 1203 and 1205.

For example, the sensing unit of each of the X-ray detectors 1203 and 1205 may be a gyroscope sensor, an IMU, an accelerometer, GPS sensor, and a magnetometer, or the like.

The pieces of information related with movements of the X-ray detectors 1203 and 1205 may be information indicating moving directions, moving distances, or moving angles of the X-ray detectors 1203 and 1205 which have been sensed based on the respective pieces of reference position information of the X-ray detectors 1203 and 1205.

In this case, since the pieces of information related to the orientation of the X-ray detectors 1203 and 1205 according to movements of the X-ray detectors 1203 and 1205 may be sensed using any of various sensors according to any of various methods that are widely used in the art, a method of sensing the pieces of position variation information of the X-ray detectors 1203 and 1205 according to movements of the X-ray detectors 1203 and 1205 is not limited to a specific method.

In this case, the position vectors $P_1$ and $P_2$ of the X-ray detectors 1203 and 1205 may be acquired using the position vector $P_3$ of the table type receptor 290, which is the initial position information of each of the X-ray detectors 1203 and 1205, and the respective pieces of position variation information received from the X-ray detectors 1203 and 1205.

The moving directions, the moving distances, or the moving angles of the X-ray detectors 1203 and 1205 may be calculated in order to acquire the respective pieces of information related to the orientation of the X-ray detectors 1203 and 1205 based on the respective pieces of reference position information of the X-ray detectors 1203 and 1205. During this calculation, an error may be generated.

In this connection, the X-ray apparatus 500 may reset the reference position information of each of the X-ray detectors 1203 and 1205, which is the position information of the table type receptor 290, every time any of the X-ray detectors 1203 and 1205 is inserted into the table type receptor 290, thereby minimizing the number of accumulated errors which occur in the calculation performed to acquire the information related to the orientation of each of the X-ray detectors 1203 and 1205.

The reference orientation information used in acquiring the information related to the orientation of each of the X-ray detector, is reset when the X-ray detector is coupled to a stand type receptor or a table type receptor.

Figure 10:
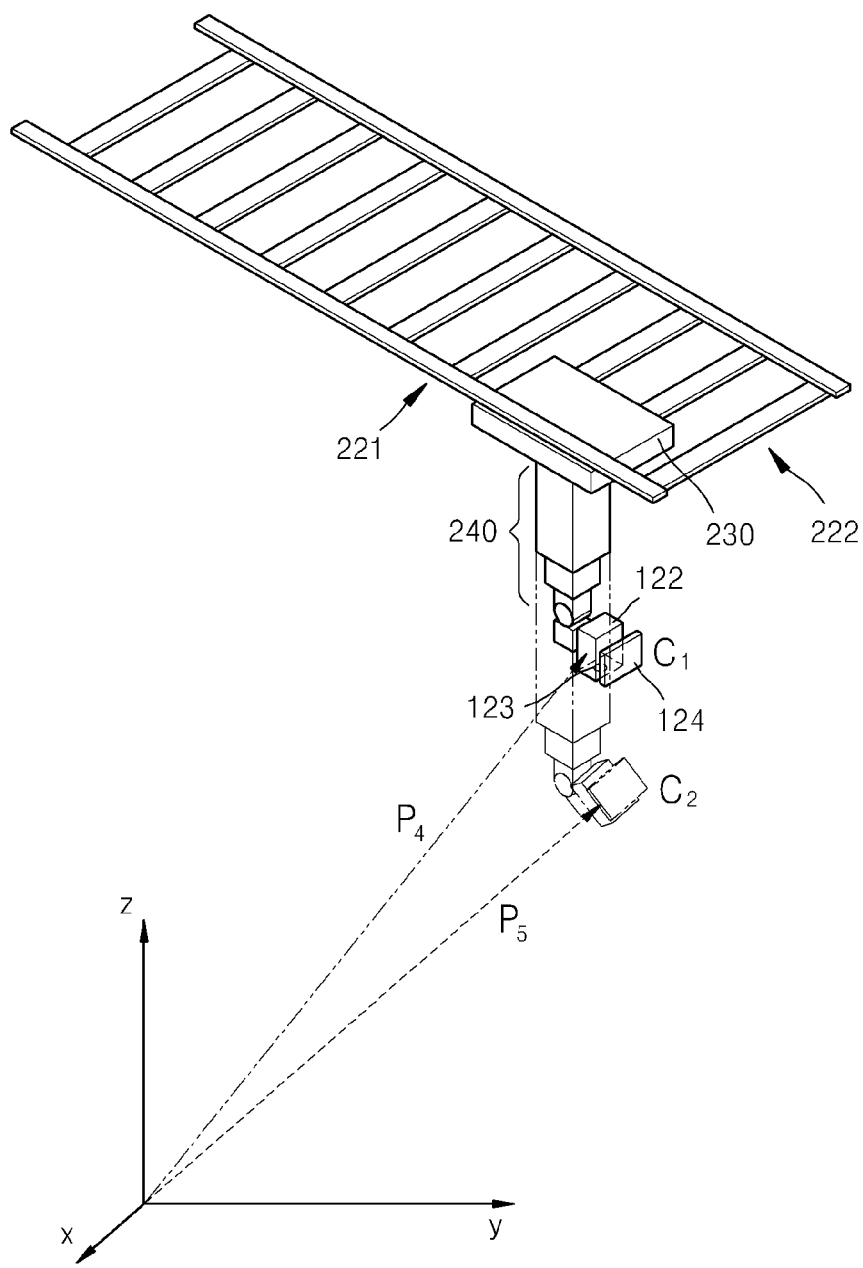
FIG. 10 illustrates an example in which the X-ray apparatus of FIG. 5 acquires position information of an X-ray radiation unit included therein.

FIG. 10 illustrates an example in which the X-ray apparatus of FIG. 5 acquires position information of an X-ray radiation unit included therein.

The X-ray radiation unit 510 may include the X-ray source 122 and/or the collimator 123.

As illustrated in FIG. 10, the X-ray source 122 in the X-ray photographing space may move to various positions $C_1$ and $C_2$ along the first and second guide rails 221 and 222 which are disposed at a certain angle. In other words, the X-ray source 122 may rotate and move in a front direction, a rear direction, a left direction, a right direction, an up direction, or a down direction or at a certain angle. The X-ray source 122 may also move in an up direction or a down direction through the post frame 240 fixed to the moving carriage 230, in the X-ray photographing space. The collimator 123 may move according to the moving of the X-ray source 122.

As illustrated in FIG. 10, the position information of the X-ray radiation unit 510 may be a position vector of the center of the X-ray radiation unit 510 in a global coordinate system that is expressed as an inertial frame in which an arbitrary location within an X-ray photographing space is the origin.

For example, when the X-ray radiation unit 510 is located at the position $C_1$, a position vector $P_4$ of the center of the X-ray radiation unit 510 may be acquired as the position information of the X-ray radiation unit 510. On the other hand, when the X-ray radiation unit 510 is located at the position $C_2$, a position vector $P_5$ of the center of the X-ray radiation unit 510 may be acquired as the position information of the X-ray radiation unit 510.

The position vector $P_4$ and the position vector $P_5$ may be directly acquired by the X-ray apparatus 500 by using any of various sensors or apparatuses.

In this case, since a position vector of an object within an X-ray photographing space may be acquired using any of various sensors or apparatuses according to any of various methods, such as methods of using light, electromagnetic waves, sound waves, a magnetic field, and an electric field, a method of acquiring the position vector of the X-ray radiation unit 510 is not limited to a specific method.

Figure 11:
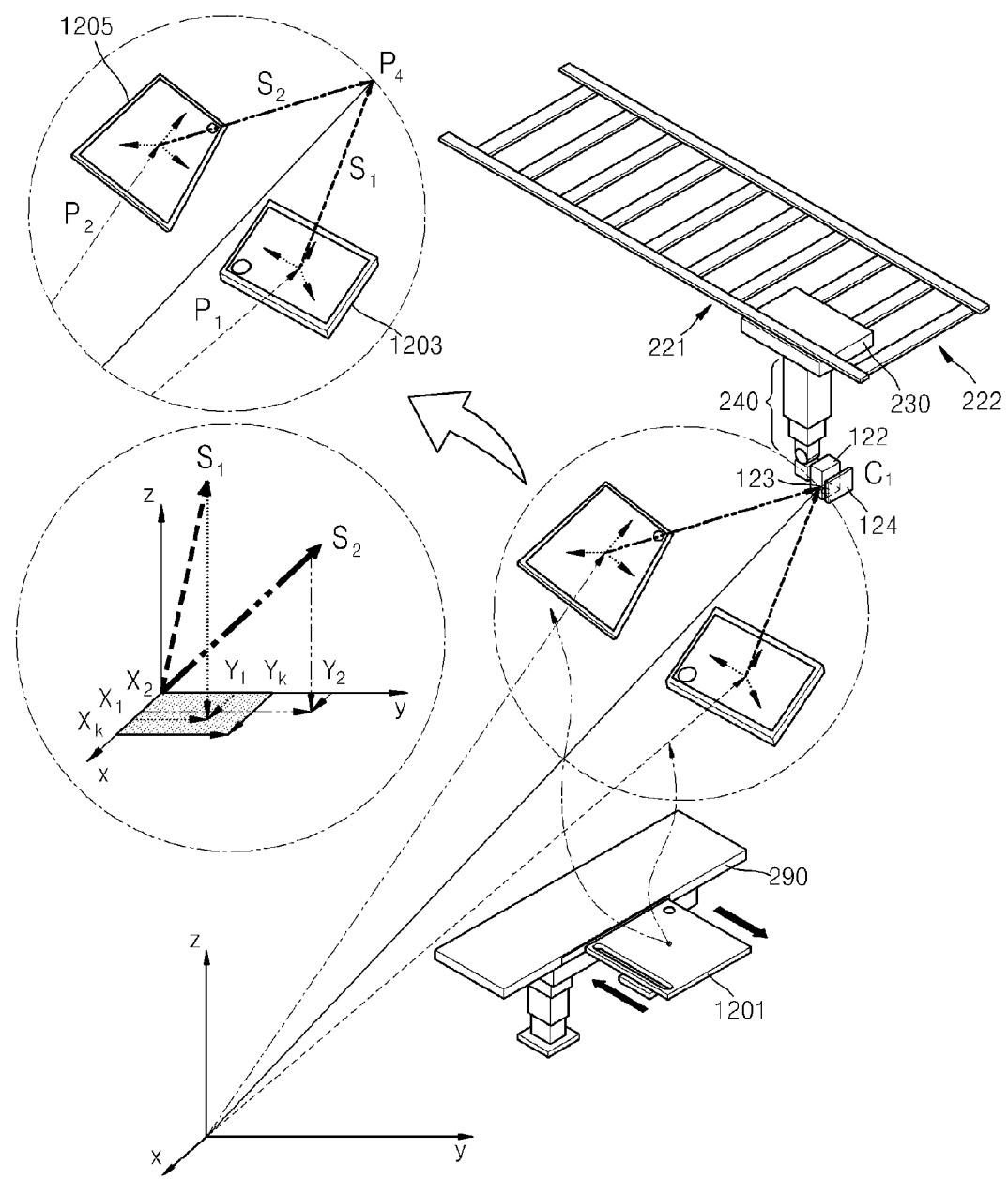
FIG. 11 illustrates an example in which the X-ray apparatus of FIG. 5 selects the X-ray detector based on position information of the X-ray radiation unit included therein and position information of the X-ray detector.

FIG. 11 illustrate an example in which the X-ray apparatus of FIG. 5 selects the X-ray detector based on position information of the X-ray radiation unit included therein and position information of the X-ray detector;

The X-ray apparatus may select the X-ray detector when a difference between lengths of the position information of the X-ray radiation unit and the position information of the X-ray detector is included in a predetermined range. In this case, the main control unit may determine a relationship between the position information of the X-ray radiation unit and the position information of the X-ray detector.

As illustrated in FIG. 11, the position information of the X-ray radiation unit may be a position vector of the X-ray radiation unit in a global coordinate system expressed as an inertial frame in which an arbitrary location within an X-ray photographing space is the origin and the position information of the X-ray detector may be a position vector of the X-ray detector in the global coordinate system.

In this case, The X-ray apparatus may select the X-ray detector based on the position vector of the X-ray radiation unit and the position vector of the X-ray detector.

As illustrated in FIG. 11, when the X-ray radiation unit 510 is located at the position $C_1$ within the X-ray photographing space, the first position vector of the X-ray radiation unit 510 may be the position vector $P_4$ of the center of the X-ray radiation unit 510.

The second position vectors of the X-ray detectors 1203 and 1205 may be the position vector $P_1$ of the center of the X-ray detector 1203 and the position vector $P_2$ of the center of the X-ray detector 1205, respectively.

When a relative vector which is a difference between the first position vector and each of the second position vector is less than or equal to a predetermined value, an X-ray detector corresponding to the second position vector may be selected. On the other hand, a signal for activating the X-ray detector corresponding to the second position vector may be generated.

For example, the case where the relative vector is less than or equal to the predetermined value may include both a case where the magnitude of the relative vector is less than or equal to the predetermined value and a case where each coordinate value of the relative vector is less than or equal to the predetermined value.

As illustrated in FIG. 11, the relative vector, which is the difference between the first position vector and the second position vector, satisfies the condition of $\{(X,Y)|0<x<X_K, 0<y<Y_K\}$, an X-ray detector corresponding to the second position vector $P_1$ may be selected. A signal for activating the X-ray detector corresponding to the second position vector $P_1$ may be generated.

As illustrated in FIG. 11, since an X-coordinate value $X_1$ and a Y-coordinate value $Y_1$ of a relative vector $S_1$, which is a difference between the first position vector $P_4$ and the second position vector $P_1$, satisfy the condition of $\{(X,Y)|0<x<X_K, 0<y<Y_K\}$, X-ray detector 1203 may be selected. On the other hand, a signal for activating the X-ray detector 1203 may be generated.

On the other hand, since an X-coordinate value $X_2$ and a Y-coordinate value $Y_2$ of a relative vector $S_2$, which is a difference between the first position vector $P_4$ and the second position vector $P_2$, do not satisfy the condition of $\{(X,Y)|0<x<X_K, 0<y<Y_K\}$, X-ray detector 1205 is not selected. And, a signal for activating the X-ray detector 1205 is not generated.

Figure 12:
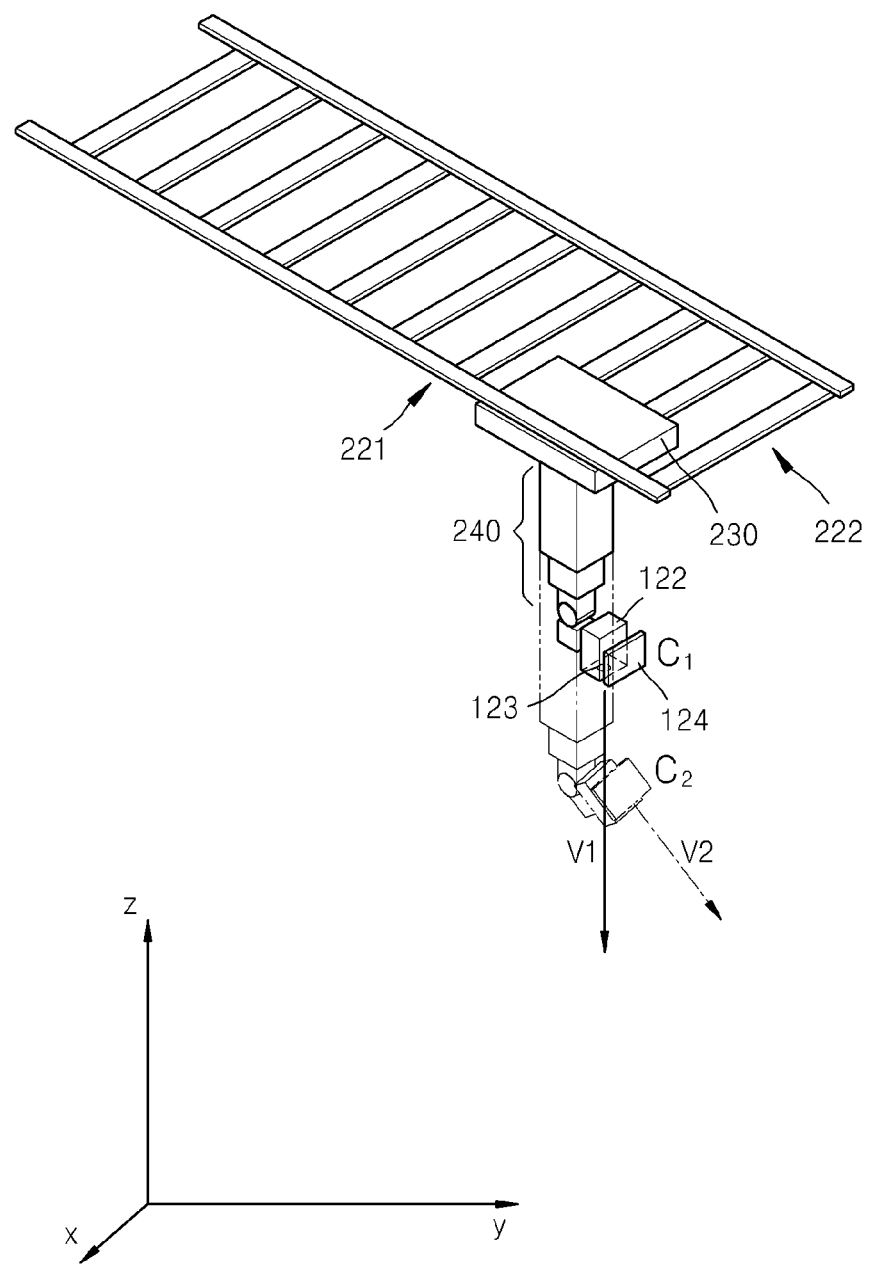
FIG. 12 illustrates an example in which the X-ray apparatus of FIG. 5 acquires directional information of an X-ray radiation unit included therein.

FIG. 12 illustrates an example in which the X-ray apparatus of FIG. 5 acquires directional information of an X-ray radiation unit included therein;

The directional information of the X-ray radiation unit may be an information related to a directional orientation of the X-ray radiation unit.

As illustrated in FIG. 12, the directional information of the X-ray radiation unit 510 may be normal vectors $V_1$ and $V_2$ of one surface of the X-ray radiation unit 510.

For example, when the X-ray radiation unit 510 is located at the position $C_1$, the normal vector $V_1$ of one surface of the X-ray radiation unit 510 may be acquired as the directional information of the X-ray radiation unit 510. On the other hand, when the X-ray radiation unit 510 is located at the position $C_2$, the normal vector $V_2$ of the one surface of the X-ray radiation unit 510 may be acquired as the directional information of the X-ray radiation unit 510.

Figure 13:
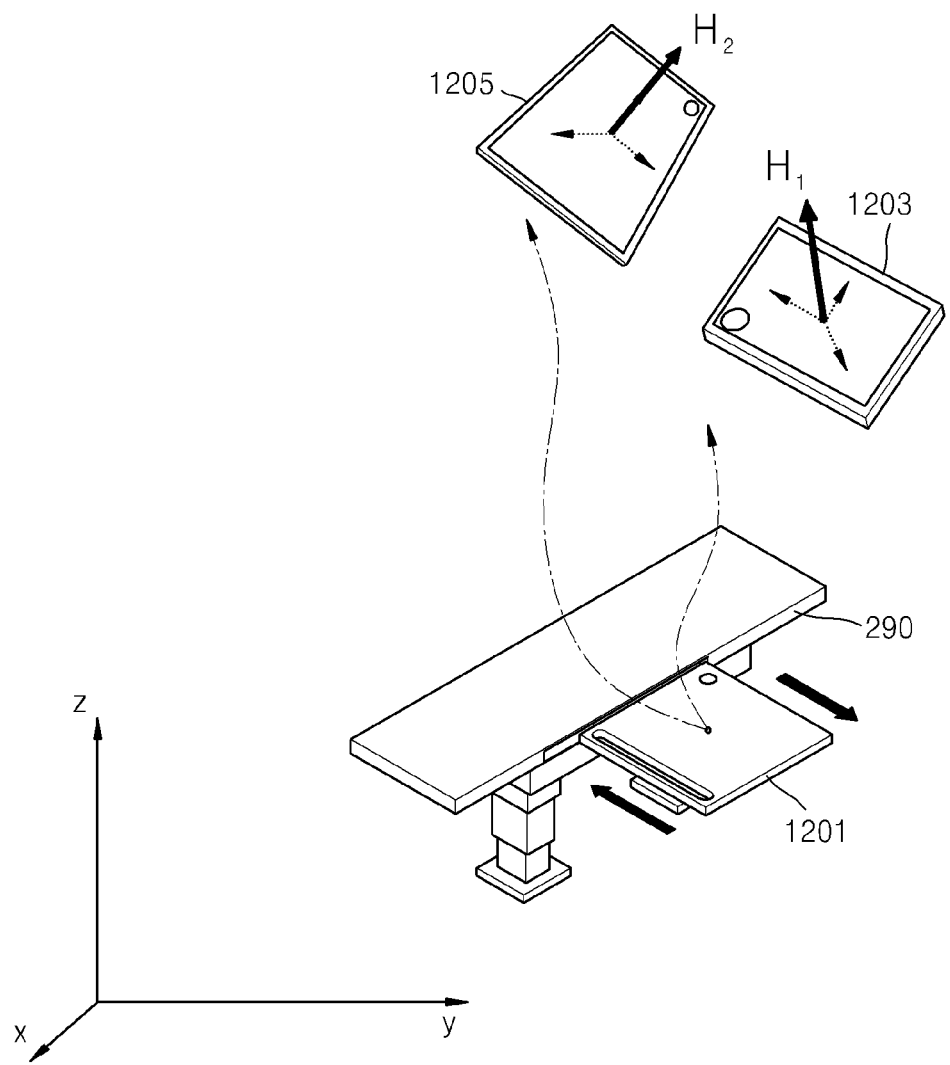
FIG. 13 illustrates an example in which the X-ray apparatus of FIG. 5 acquires directional information of an X-ray detector.

FIG. 13 illustrates an example in which the X-ray apparatus of FIG. 5 acquires directional information of an X-ray detector.

The directional information of the X-ray detector may be information related to a facing direction of the X-ray radiation unit.

As illustrated in FIG. 13, the respective pieces of directional information of the X-ray detectors 1203 and 1205 may be a normal vector $H_1$ of one surface of the X-ray detector 1203 and a normal vector $H_2$ of one surface of the X-ray detector 1205.

For example, a normal vector of an X-ray detector may be a direction perpendicular to a plane irradiated by an X-ray. The normal vector may also be a direction perpendicular to a plane formed by a photodetecting substrate 410.

Figure 14:
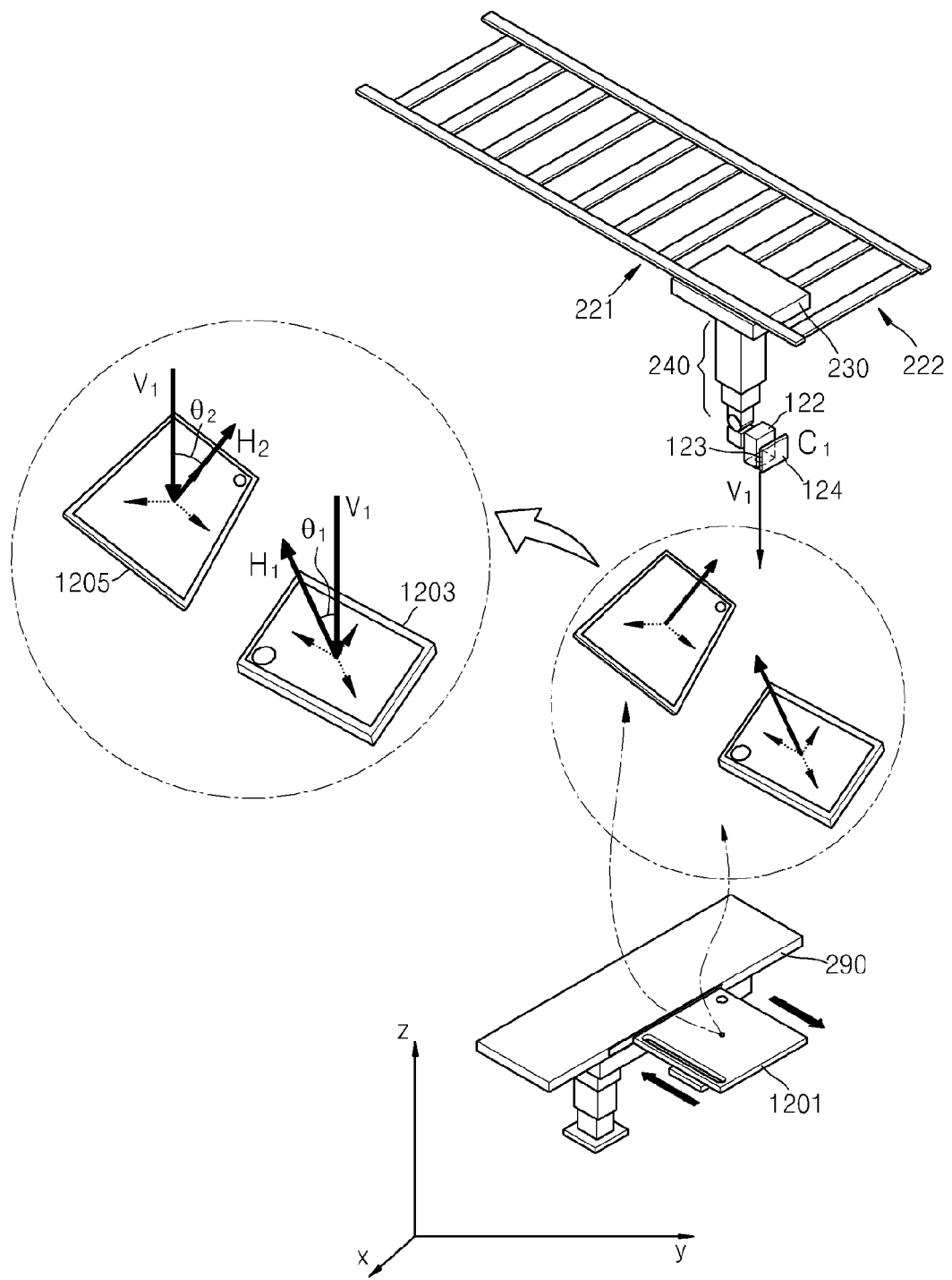
FIG. 14 illustrates an example in which the X-ray apparatus of FIG. 5 selects the X-ray detector based on directional information of the X-ray radiation unit included therein and directional information of the X-ray detector.

FIG. 14 illustrates an example in which the X-ray apparatus of FIG. 5 selects the X-ray detector based on directional information of the X-ray radiation unit included therein and directional information of the X-ray detector.

The X-ray apparatus may select the X-ray detector when a difference between angles of the directional information of the X-ray radiation unit indicating a directional orientation of the X-ray and the directional information of the X-ray detector indicating a facing direction of the X-ray radiation unit is included in a predetermined range. In this case, the main control unit may determine a relationship between the directional information of the X-ray radiation unit and the directional information of the X-ray detector.

For example, as illustrated in FIG. 14, the directional information of the X-ray radiation unit may be a first normal vector on a surface of the X-ray radiation unit, and the directional information of the X-ray detector may be a second normal vector on a surface of the X-ray detector.

In this case, the X-ray apparatus may select the X-ray detector based on the first normal vector of the X-ray radiation unit and the second normal vector of the X-ray detector.

As illustrated in FIG. 14, when the X-ray radiation unit 510 is located at the position C1 within the X-ray photographing space, the first normal vector of the X-ray radiation unit 510 may be the normal vector V1 of one surface of the X-ray radiation unit 510.

The second normal vectors of the X-ray detectors 1203 and 1205 may be the normal vector H1 of the one surface of the X-ray detector 1203 and the normal vector H2 of the one surface of the X-ray detector 1205, respectively.

In this case, when a difference between angles of the first and second normal vector is included in a predetermined range (e.g., less than 30 deg, or less than 15 deg, as desired), an X-ray detector corresponding to the second normal vector may be selected. On the other hand, a signal for activating the X-ray detector corresponding to the second normal vector may be generated.

As illustrated in FIG. 14, since an angle difference θ1 between the first normal vector V1 and the second normal vector H1 is included in the range of less than 30 deg, the X-ray detector 1203 corresponding to the second normal vector H1 may be selected. On the other hand, a signal for activating the X-ray detector 1203 corresponding to the second normal vector H1 may be generated.

On the other hand, since an angle difference θ2 between the first normal vector V1 and the second normal vector H2 is not included in the range of less than 30 deg, the X-ray detector 1205 corresponding to the second normal vector H2 may not be selected.

Figure 15:
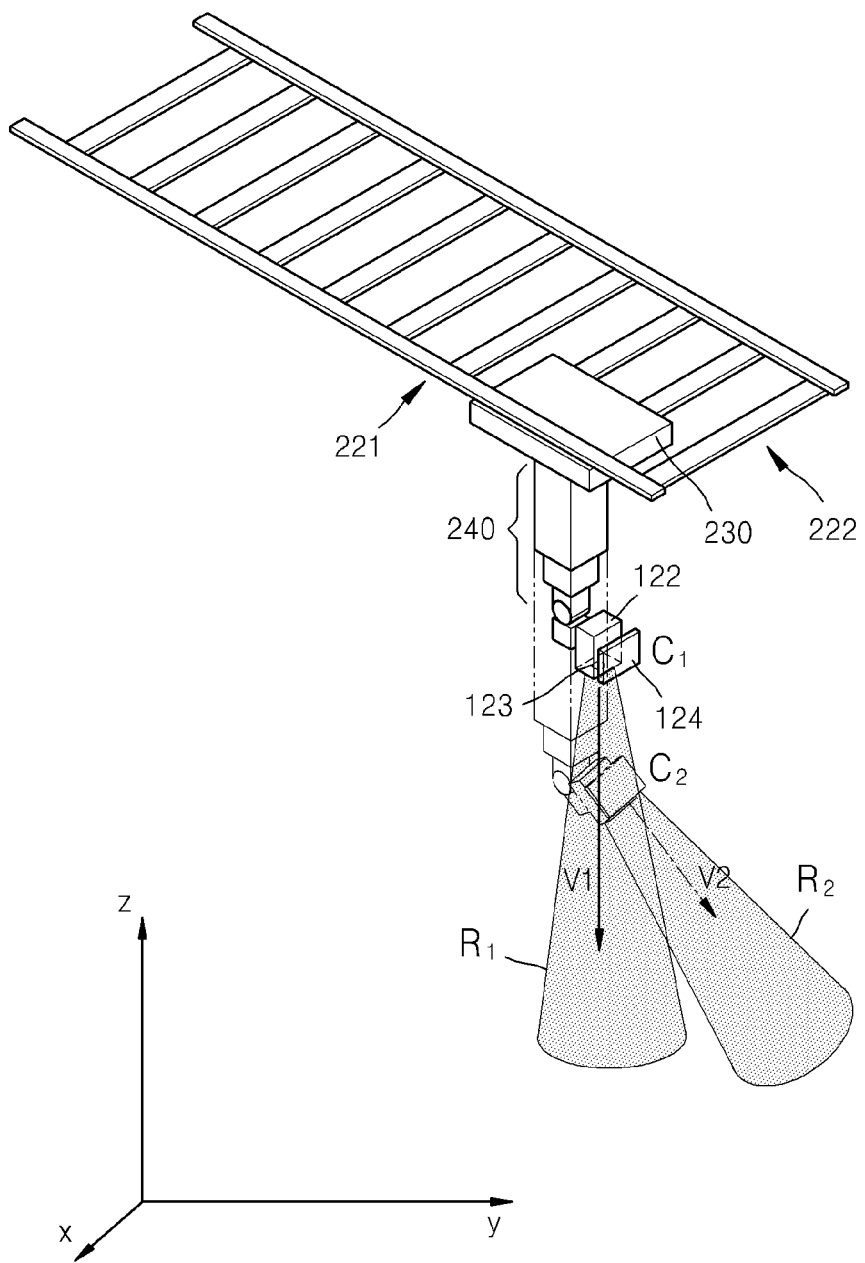
FIG. 15 illustrates an example in which the X-ray apparatus of FIG. 5 acquires directional information of an X-ray radiation unit included therein.

FIG. 15 illustrates an example in which the X-ray apparatus of FIG. 5 acquires directional information of an X-ray radiation unit included therein.

The directional information of the X-ray radiation unit may be an information related to an X-ray irradiation region.

As illustrated in FIG. 15, the directional information of the X-ray radiation unit 510 may be volume vector groups $R_1$ and $R_2$ corresponding to respective X-ray irradiation regions at the positions $C_1$ and $C_2$.

The volume vector groups $R_1$ and $R_2$ may be formed with 3D shapes on the regions irradiated by X-rays respectively radiated by the X-ray radiation unit 510 at the positions $C_1$ and $C_2$.

For example, as illustrated in FIG. 15, the volume vector groups $R_1$ and $R_2$ may include the normal vectors $V_1$ and $V_2$ of one surface of the X-ray radiation unit 510 indicating directional orientation of the X-ray at the positions $C_1$ and $C_2$, respectively.

Figure 16:
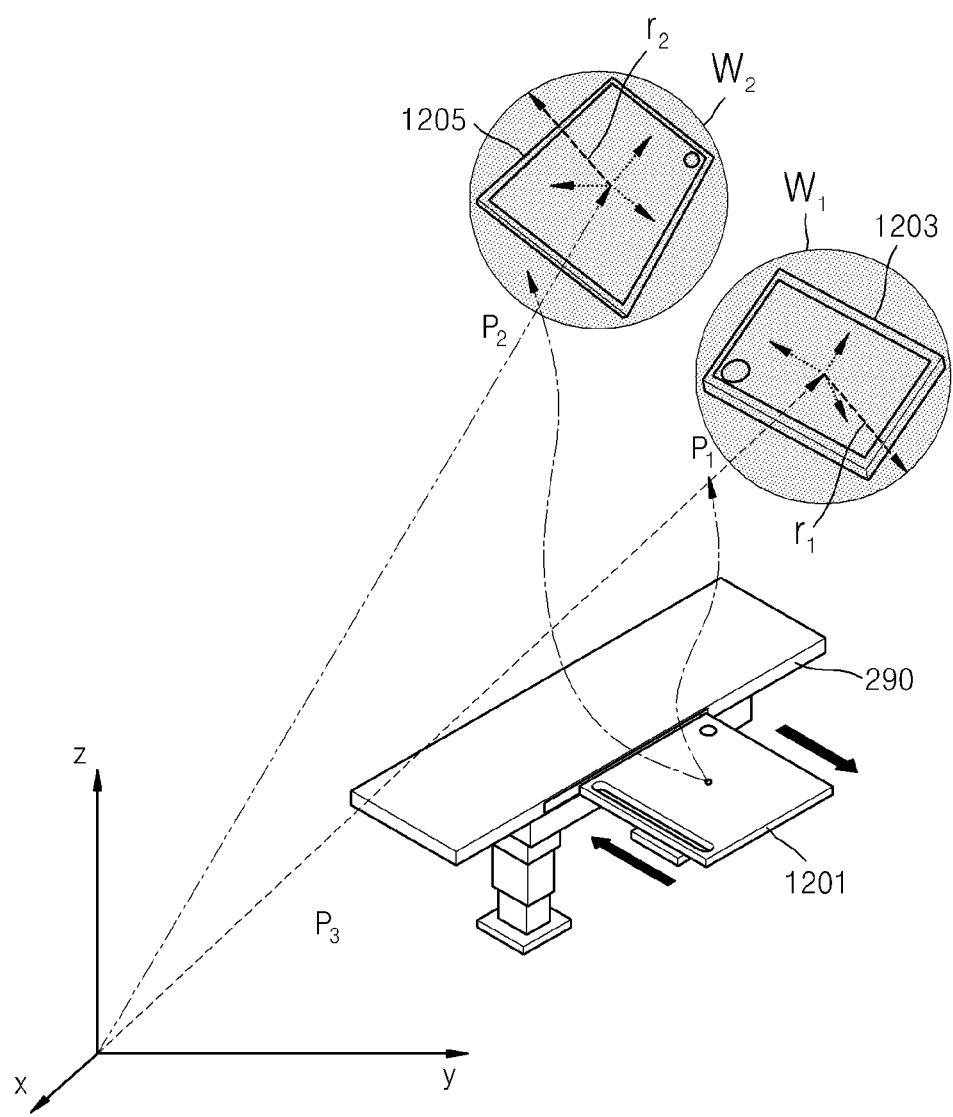
FIG. 16 illustrates an example in which the X-ray apparatus of FIG. 5 acquires position information of an X-ray detector.

FIG. 16 illustrates an example in which the X-ray apparatus of FIG. 5 acquires position information of an X-ray detector.

As illustrated in FIG. 16, the X-ray detectors 1201, 1203, and 1205 may be freely dispersed within a single X-ray photographing space, the X-ray apparatus 500 acquires respective position information of X-ray detectors 1201, 1203, and 1205.

For example, the position information of the X-ray detector includes a position vector of the X-ray detector or a volume vector group including a plurality of position vectors existing within a predetermined distance from the position vector of the X-ray detector.

As illustrated in FIG. 16, respective pieces of position information of the X-ray detectors 1203 and 1205 may be position vectors $P_1$ and $P_2$ of the respective the X-ray detectors 1203 and 1205 in a global coordinate system that is expressed as an inertial frame in which an arbitrary location within an X-ray photographing space is the origin.

Also, as illustrated in FIG. 16, the respective pieces of position information of the X-ray detectors 1203 and 1205 may be volume vector groups $W_1$ and $W_2$ including of a plurality of position vectors existing within predetermined distances $r_1$ and $r_2$, respectively, from the position vectors $P_1$ and $P_2$ of the respective centers of the X-ray detectors 1203 and 1205.

The volume vector groups $W_1$ and $W_2$ may have predetermined 2D shapes having areas of about 125% to about 150% in comparison with the respective areas of the X-ray detectors 1203 and 1205, respectively.

In addition, the volume vector groups $W_1$ and $W_2$ may have larger areas than respective regions of the X-ray detectors 1203 and 1205 from which X-rays are actually detected. For example, the predetermined 2D shape may be a circle, an oval, or a polygon (e.g., a square).

In this case, the shapes of the volume vector groups $W_1$ and $W_2$ may be spheres as illustrated in FIG. 10. Although not shown, the shape of each of the volume vector groups $W_1$ and $W_2$ may be a 2D geometric shape, such as a circle, an oval, or a polygon (e.g., a square), or a 3D geometric shape, such as a sphere, an ellipsoid, or a polyhedron.

Figure 17:
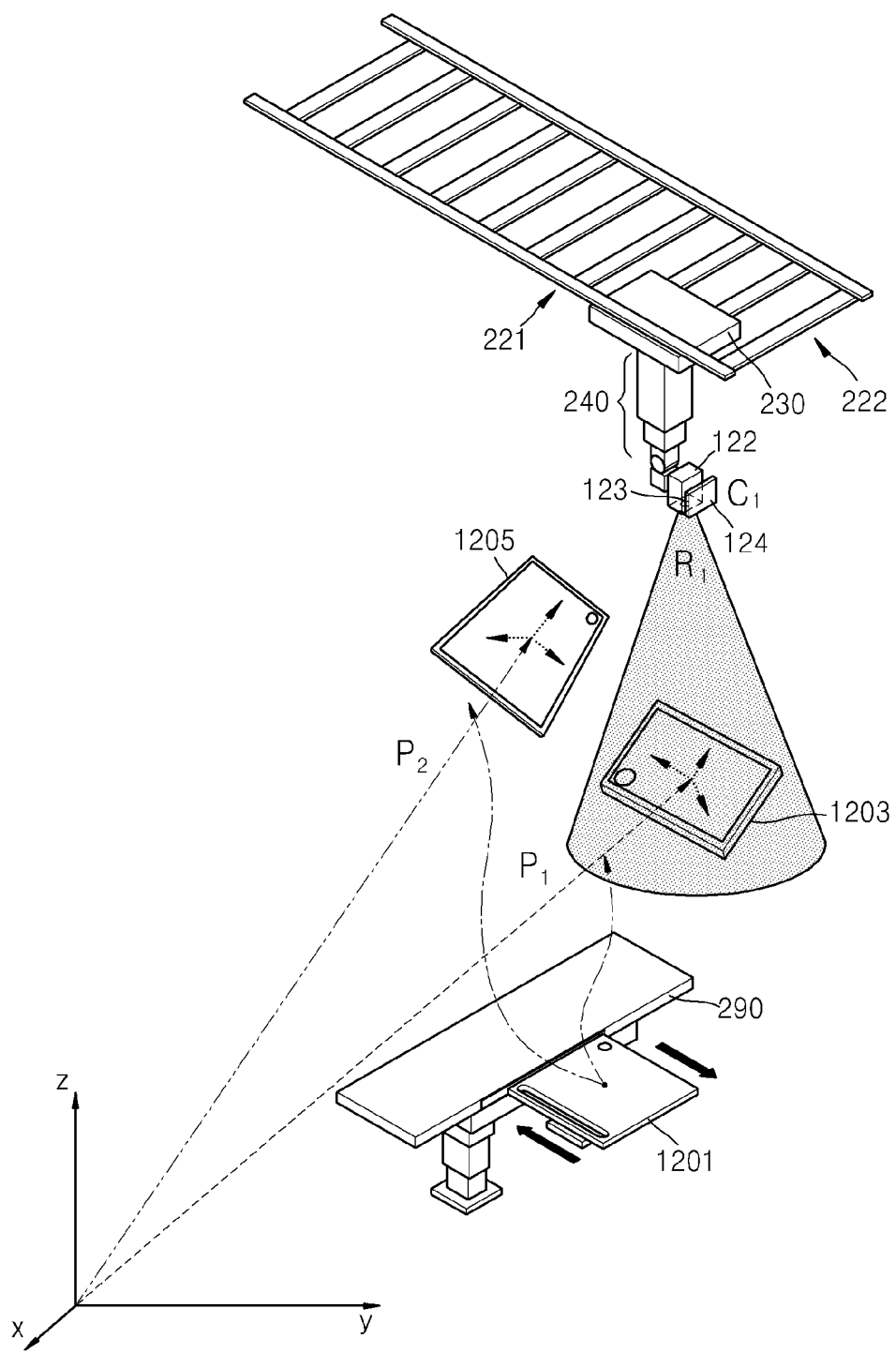
FIGS. 17-18 illustrate various examples in which the X-ray apparatus of FIG. 5 select the X-ray detector based on directional information of the X-ray radiation unit included therein and position information of the X-ray detector.
Figure 18:
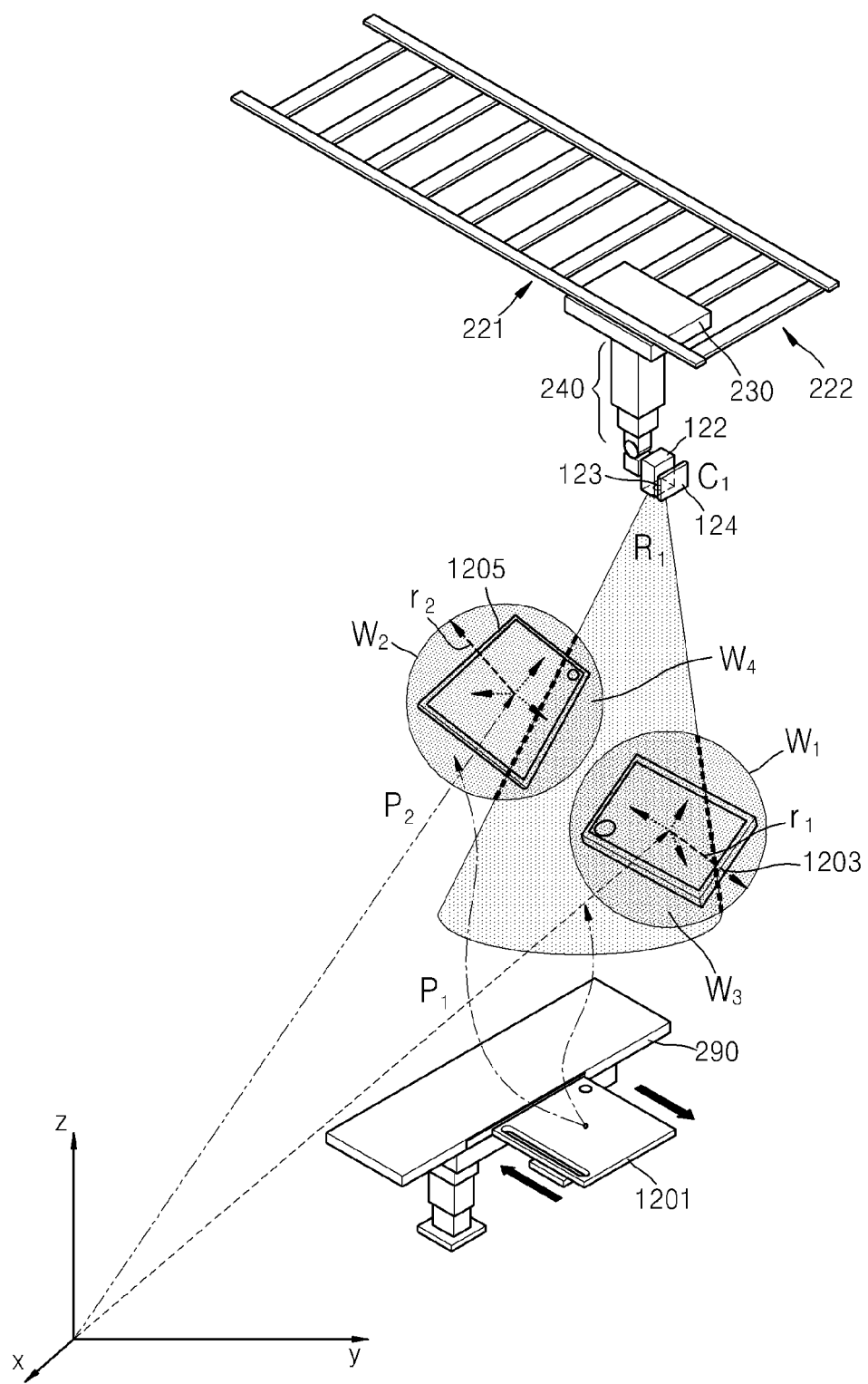

FIGS. 17-18 illustrate various examples in which the X-ray apparatus of FIG. 5 select the X-ray detector based on directional information of the X-ray radiation unit included therein and position information of the X-ray detector.

The X-ray apparatus may select the X-ray detector when the directional information of the X-ray radiation unit corresponding to X-ray irradiation regions is adjacent to the position information of the X-ray detector.

In this case, the main control unit may determine a relationship between the directional information of the X-ray radiation unit and the position information of the X-ray detector.

As illustrated in FIG. 17, when the X-ray radiation unit 510 is located at the position $C_1$ within the X-ray photographing space, the directional information of the X-ray radiation unit 510 may be the volume vector group $R_1$ corresponding to the X-ray irradiation region. And the position information of the X-ray detectors 1203 and 1205 may be the position vector $P_1$ of the X-ray detector 1203 and the position vector $P_2$ of the X-ray detector 1205, respectively.

In this case, the X-ray apparatus may select the X-ray detector based on the volume vector group of the X-ray radiation unit and the position vectors of the X-ray detectors 1203 and 1205. On the other hand, In this case, the X-ray apparatus may generate the signal for activating the X-ray detector based on the volume vector group of the X-ray radiation unit and the position vectors of the X-ray detectors 1203 and 1205.

For example, when the position vector of the X-ray detector is included in the volume vector group of the X-ray radiation unit, selects the X-ray detector corresponding to the position vector may be selected. On the other hand, the signal for activating the X-ray detector corresponding to the position vector may be generated.

As illustrated in FIG. 17, since the second position vector $P_1$ is included in the volume vector group $R_1$, the X-ray detector 1203 corresponding to the second position vector $P_1$ may be selected. On the other hand, a signal for activating the X-ray detector 1203 corresponding to the second position vector $P_1$ may be generated.

On the other hand, since the second position vector $P_2$ is not included in the volume vector group $R_1$, a signal for activating the X-ray detector 1205 may not be selected.

As illustrated in FIG. 18, when the X-ray radiation unit 510 is located at the position $C_1$ within the X-ray photographing space, the directional information of the X-ray radiation unit 510 may be the volume vector group $R_1$ corresponding to the X-ray irradiation region. And the position information of the X-ray detectors 1203 and 1205 may be the volume vector groups $W_1$ and $W_2$ including a plurality of position vectors existing within the predetermined distances $r_1$ and $r_2$ from the position vectors $P_1$ and $P_2$ of the respective centers of the X-ray detectors 1203 and 1205, respectively.

In this case, the X-ray apparatus may select the X-ray detector based on the first volume vector group of the X-ray radiation unit and the second volume vector groups of the X-ray detectors 1203 and 1205. On the other hand, the X-ray apparatus may generate the signal for activating the X-ray detector based on the first volume vector group of the X-ray radiation unit and the second volume vector groups of the X-ray detectors 1203 and 1205.

For example, when a ratio of the number of position vectors in the second volume vector group with respect to the number of a plurality of position vectors included in the first volume vector group is equal to or greater than a predetermined value ($0<k<1$, real number, i.e, $k=0.7$,) the X-ray detector corresponding to the second volume vector group may be selected. On the other hand, a signal for activating the X-ray detector corresponding to the second volume vector group may be generated.

As illustrated in FIG. 18, since the size of a group $W_3$ of a plurality of position vectors existing within both the first volume vector group $R_1$ and the second volume vector group $W_1$ is at least 0.7 of the size of the second volume vector group $W_1$, the X-ray detector 1203 corresponding to the second volume vector group $W_1$ may be selected. On the other hand, a signal for activating the X-ray detector 1203 corresponding to the second volume vector group $W_1$ may be generated.

On the other hand, since the size of a group $W_4$ of a plurality of position vectors existing within both the first volume vector group $R_1$ and the second volume vector group $W_2$ is less than 0.7 of the size of the second volume vector group $W_2$, the X-ray detector 1205 corresponding to the second volume vector group $W_2$ may not be generated.

Figure 19:
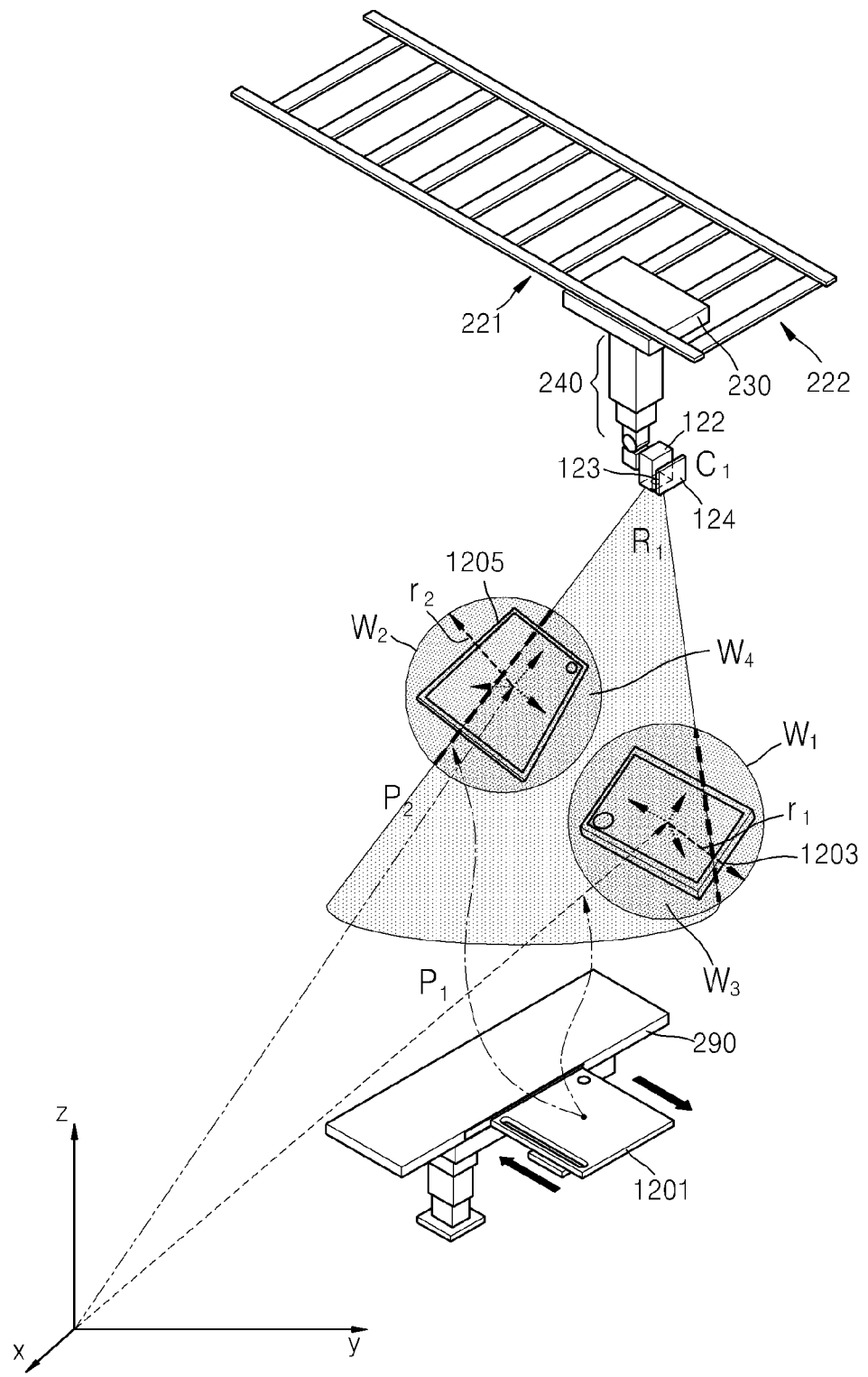
FIG. 19 illustrates an example in which the X-ray apparatus of FIG. 5 selects a plurality of X-ray detectors based on orientation information of the X-ray radiation unit included therein and orientation information of the X-ray detector

FIG. 19 illustrates an example in which the X-ray apparatus of FIG. 5 selects a plurality of X-ray detectors based on orientation information of the X-ray radiation unit included therein and orientation information of the X-ray detector.

For example, orientation information of the X-ray radiation unit 510 includes at least one of selected from position information of the X-ray radiation unit 510 and directional information of the X-ray radiation unit 510 and orientation information of an X-ray detector includes at least one of selected from position information of the X-ray detector and directional information of the X-ray detector.

As illustrated in FIG. 18, the X-ray apparatus may select the X-ray detector based on the directional information of the X-ray radiation unit and the position information of the X-ray detector.

As illustrated in FIG. 19, the X-ray apparatus may select the X-ray detector based on the first volume vector group $R_1$ of the X-ray radiation unit 510 corresponding to the directional information of the X-ray radiation unit 510 and the second volume vector groups $W_1$ and $W_2$ of the X-ray detectors 1203 and 1205 corresponding to the position information of the X-ray detectors.

For example, when a ratio of the number of position vectors in the second volume vector group with respect to the number of a plurality of position vectors included in the first volume vector group is equal to or greater than a predetermined value (0<k<1, real number, i.e, k=0.7,) the X-ray detector corresponding to the second volume vector group may be selected.

As illustrated in FIG. 19, since the size of a group $W_3$ of a plurality of position vectors existing within both the first volume vector group $R_1$ and the second volume vector group $W_1$ is at least 0.7 of the size of the second volume vector group $W_1$, the X-ray detector 1203 corresponding to the second volume vector group $W_1$ may be selected. On the other hand, a signal for activating the X-ray detector 1203 corresponding to the second volume vector group $W_1$ may be generated.

Also, as illustrated in FIG. 19, since the size of a group $W_4$ of a plurality of position vectors existing within both the first volume vector group $R_1$ and the second volume vector group $W_2$ is at least 0.7 of the size of the second volume vector group $W_2$, the X-ray detector 1205 corresponding to the second volume vector group $W_2$ may be selected. On the other hand, a signal for activating the X-ray detector 1205 corresponding to the second volume vector group $W_2$ may be generated.

In other words, the X-ray detectors 1203 and 1205 may be both selected, or activated. In this case, at least one X-ray detector, namely, the X-ray detectors 1203 and 1205, to be used in photographing may be selected by the user's input from among a plurality of X-ray detectors.

Figure 20:
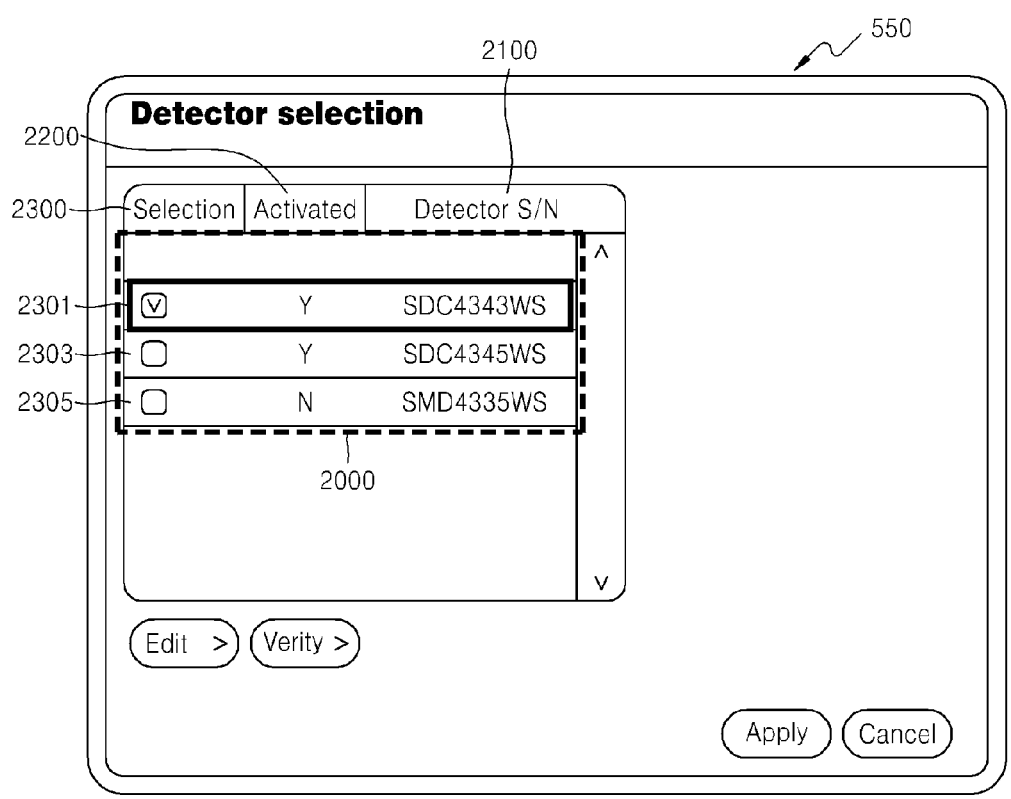
FIG. 20 illustrates an example in which the X-ray apparatus of FIG. 5 displays information about a plurality of X-ray detectors selectable by a user on an output unit included in the X-ray apparatus.

FIG. 20 illustrates an example in which the X-ray apparatus of FIG. 5 displays information about a plurality of X-ray detectors selectable by a user on an output unit included in the X-ray apparatus.

For example, as illustrated in FIG. 20, a UI 2000 for receiving a user's selection of at least one X-ray detector from among a plurality of X-ray detectors may be output.

The UI 2000 may include respective pieces of information about a plurality of X-ray detectors 2301, 2303, and 2305, i.e., X-ray detectors which may be used to X-ray an object. The respective pieces of information about the X-ray detectors 2301, 2303, and 2305 may be arranged according to a predetermined arrangement criterion and then output.

For example, the information about each of the X-ray detectors 2301, 2303, and 2305 may include unique information 2100 of each of the X-ray detectors 2301, 2303, and 2305. In detail, the unique information 2100 may include at least one selected from a serial number (SN) of each of the X-ray detectors 2301, 2303, and 2305 and an Internet Protocol (IP) address thereof. In detail, the SN of each of the X-ray detectors 2301, 2303, and 2305 is a unique identifier given during the manufacture of each of the X-ray detectors 2301, 2303, and 2305. The IP address of each of the X-ray detectors 2301, 2303, and 2305 may include an IP address value that is to be used when each of the X-ray detectors 2301, 2303, and 2305 and an access point (AP) communicate with each other.

The information about each of the X-ray detectors 2301, 2303, and 2305 may include specification information of each of the X-ray detectors 2301, 2303, and 2305. In detail, the specification information may include at least one selected from the size of each of the X-ray detectors 2301, 2303, and 2305 and the type of a receptor with which each of the X-ray detectors 2301, 2303, and 2305 is combinable. An X-ray detector adequate for X-ray photographing may have different sizes and shapes according to parts of an object to be photographed. Accordingly, the sizes of the X-ray detectors 2301, 2303, and 2305 may be a criterion on which a user selects an X-ray detector suitable for photographing. In addition, when a user wants to combine the X-ray detectors 2301, 2303, and 2305 to a predetermined receptor, the type of a receptor with which the X-ray detectors 2301, 2303, and 2305 are combinable may be a criterion on which a user selects an X-ray detector suitable for photographing.

The specification information of each of the X-ray detectors 2301, 2303, and 2305 is not limited to the sizes of the X-ray detectors 2301, 2303, and 2305 and the type of a receptor with which the X-ray detectors 2301, 2303, and 2305 are combinable.

For example, the predetermined arrangement criterion may be a distance proximity to the X-ray radiation unit 510, the sizes of the X-ray detectors 2301, 2303, and 2305, or the like. For example, an X-ray detector which is relatively closer to the X-ray radiation unit 510 than an X-ray detector disposed on the table type receptor 290 may have a higher priority than that of the X-ray detector 1205 disposed on the table type receptor 290 when pieces of information about a plurality of X-ray detectors are output to the output unit 550. In addition, an X-ray detector having a relatively large size may have a higher priority than an X-ray detector having a relatively small size. For example, an X-ray detector having a size of 17 inch×17 inch may have a higher priority than an X-ray detector having a size of 14 inch×17 inch when pieces of information about a plurality of X-ray detectors are output to the output unit 550.

The information about each of the X-ray detectors 2301, 2303, and 2305 may further include information 2200 indicating whether each of the X-ray detectors 2301, 2303, and 2305 has been activated.

In this case, an X-ray detector that is automatically activated based on the orientation information of the X-ray radiation unit and the orientation information of the X-ray detector may have a high priority, i.e., a relatively higher priority as compared to other X-ray detectors, when pieces of information about a plurality of X-ray detectors are output to the output unit 550.

For example, as illustrated in FIG. 20, the X-ray detectors 2301 and 2303 which are automatically activated may be output in preference to the X-ray detector 2305 which has not been activated. That is, the X-ray detectors 2301 and 2303 are displayed on a top of the screen.

The UI 2000 may further include an icon 2300 for selecting an X-ray detector that is desired to be activated according to a user input.

As illustrated in FIG. 20, when a user selects the X-ray detector 2301 corresponding to an SN of SDC4343WS, the X-ray detector 2301 may be determined as the at least one X-ray detector that is to be used in photographing.

In this case, the X-ray detector 2303, which is not selected by the user's input to be used in X-ray imaging of an object, may be deactivated.

Although a plurality of X-ray detectors 2301 and 2303 positioned in certain directions from the X-ray radiation unit 510 are automatically activated, only the X-ray detector selected by a user may remain activated to be subsequently used in the X-ray imaging of an object.

Figure 21:
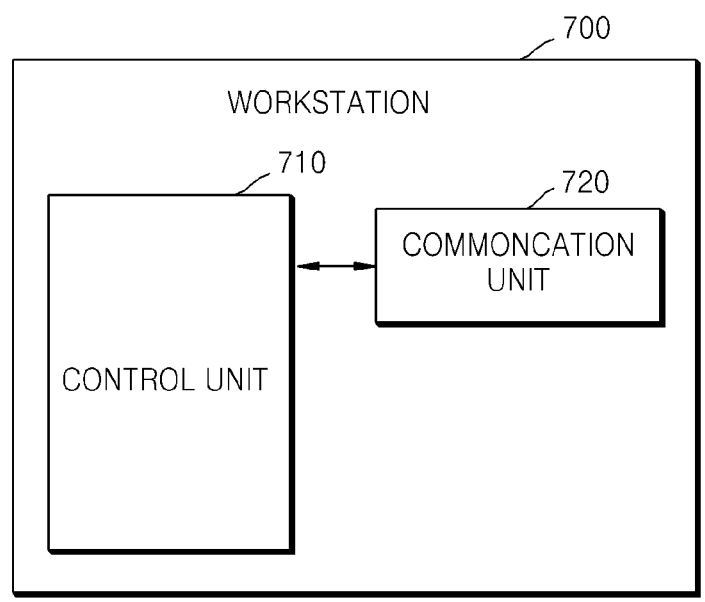
FIG. 21 is a block diagram of a workstation according to an embodiment.

FIG. 21 is a block diagram of a workstation according to an embodiment.

The workstation 700 may include a control unit 710 and a communication unit 720. The workstation 700 may further include a transmission unit (not shown), a reception unit (not shown), an output unit (not shown), and an input unit (not shown).

When the workstation 700 of FIG. 21 is included in the X-ray system 1000 of FIG. 1, the workstation 700 of FIG. 21 may correspond to the workstation 110 of FIG. 1. In detail, the control unit 710, the output unit (not shown), and the input unit (not shown) of the workstation 700 of FIG. 21 may respectively correspond to the control unit 113, the output unit 111, and the input unit 112 of the workstation 110 of FIG. 1. The communication unit 720 of the workstation 700 of FIG. 21 may communicate with the X-ray apparatus 100 of FIG. 1 by wires or wirelessly and may also communicate with an external apparatus via the network 1501 of FIG. 1. Thus, a repeated description thereof will be omitted.

The aforementioned components will now be described in detail

The control unit 710 may acquire orientation information of an X-ray radiation unit and orientation information of an X-ray detector.

For example, orientation information of the X-ray radiation unit 510 includes at least one of selected from position information of the X-ray radiation unit 510 and directional information of the X-ray radiation unit 510 and orientation information of an X-ray detector includes at least one of selected from position information of the X-ray detector and directional information of the X-ray detector.

In this case, the orientation information of the X-ray radiation unit 510 or the orientation information of the X-ray detector may be directly acquired by the control unit 710 of the workstation 700 by using any of various sensors or apparatuses.

For example, the orientation information of the X-ray radiation unit 510 or the orientation information of the X-ray detector may be acquired in real time by a camera or may be acquired using a wireless frequency.

In this case, since orientation information of an object within an X-ray photographing space may be acquired using any of various sensors or apparatuses according to various methods, such as methods of using light, electromagnetic waves, sound waves, a magnetic field, and an electric field, a method of acquiring the orientation information of the X-ray radiation unit 510 or the orientation information of the X-ray detector is not limited to a specific method.

The orientation information of the X-ray detector may also be acquired by using reference orientation information which are initial orientation information of the X-ray detector and using information related to orientation of the X-ray detector, that the communication unit 720 of the workstation 700 has received from the X-ray detector. In this case, the control unit 710 acquires the orientation information of the X-ray detector.

The reference orientation information includes at least one of selected from reference position information of the X-ray detector and reference directional information of the X-ray detector based on initial orientation of the X-ray detector.

The control unit 710 may select the X-ray detector based on the orientation information of the X-ray radiation unit included therein and the orientation information of the X-ray detector. Also, the control unit 710 may activate the X-ray detector based on the orientation information of the X-ray radiation unit included therein and the orientation information of the X-ray detector.

The communication unit 720 may transmit a signal for activating the X-ray detector or informing selection of the X-ray detector to the X-ray detector to be used for photographing.

In this case, the X-ray detector may be activated based on the signal received from the workstation via a network.

The control unit 710 may control orientation of the X-ray radiation unit, based on the orientation information of the selected X-ray detector.

An X-ray system according to an embodiment includes an X-ray apparatus including an X-ray radiation unit, an X-ray detector, and a workstation that controls the X-ray apparatus and the X-ray detector. The workstation includes a control unit and a communication unit. The control unit acquires orientation information of the X-ray radiation unit and orientation information of the X-ray detector, and controls the workstation to select the X-ray detector or generate a signal for activating the selected X-ray detector based on the orientation information of the X-ray radiation unit and the orientation information of the X-ray detector.

The communication unit transmits the signal to the X-ray detector.

The X-ray detector includes a communication unit and a detector control unit. The communication unit receives the signal from the workstation, and the detector control unit controls the X-ray detector to be activated based on the signal.

In the X-ray system, the control unit of the workstation may also control the orientation of the X-ray radiation unit, based on the orientation information of the X-ray detector.

Figure 22:
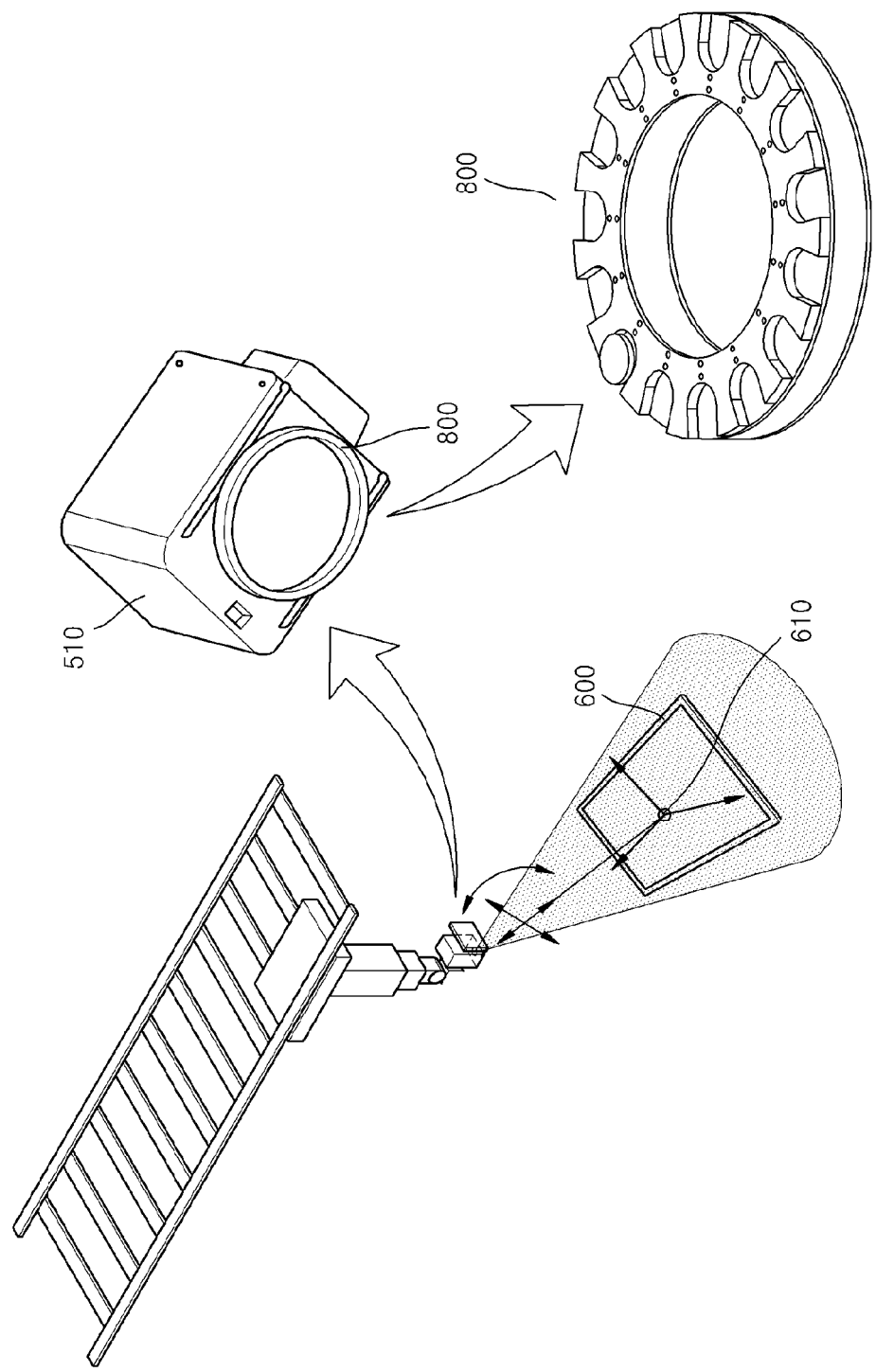
FIG. 22 illustrates an example in which the X-ray apparatus of FIG. 5 controls an orientation of an X-ray radiation unit included therein based on orientation information of the X-ray detector of FIG. 6.

FIG. 22 illustrates an example in which the X-ray apparatus of FIG. 5 controls an orientation of an X-ray radiation unit included therein based on orientation information of the X-ray detector of FIG. 6.

As illustrated in FIG. 22, the X-ray radiation unit 510 may include a magnetic field source 800, and the magnetic field source 800 may be coupled to a lower end of a collimator and radiate a magnetic field.

The magnetic field source 800 may include a ring-shaped coil and a plurality of magnets. In this case, the magnetic field source 800 may emit a magnetic field including both a magnetic field generated by the magnets and a magnetic field generated by the ring-shaped coil.

The sensor unit 610 of the X-ray detector 600 may be a magnetometer. The magnetometer 610 may include three axes and sense the intensity of a magnetic field. For example, the magnetometer 610 of the X-ray detector 600 may sense the intensity of a magnetic field emitted by the magnetic field source 800 coupled to the X-ray radiation unit 510. At this time, the detector control unit 620 of the X-ray detector 600 may acquire magnetic field information including information about the direction and size of the magnetic field sensed by the magnetometer 610.

In addition, the detector control unit 620 of the X-ray detector 600 may determine a relationship between orientations of the X-ray radiation unit 510 and the X-ray detector 600, based on the acquired magnetic field information.

For example, when a magnetic field change rate of a tangential vector of the magnetic field information is 0, the control unit 620 of the X-ray detector 600 may determine that the X-ray radiation unit 510 and the X-ray detector 600 faces each other.

At this time, information about the relationship between the orientations of the X-ray radiation unit 510 and the X-ray detector 600 determined by the X-ray detector 600 may be transmitted to the X-ray apparatus 500.

Accordingly, a user may ascertain the relationship between the orientations of the X-ray radiation unit 510 and the X-ray detector 600. In this case, the user may adjust the orientation of the X-ray radiation unit 510 that is at least one of selected from position, direction and angle of the X-ray radiation unit 510, so that the X-ray radiation unit 510 and the X-ray detector 600 face each other.

Alternatively, the control unit 520 of the X-ray apparatus 500 may automatically adjust the orientation of the X-ray radiation unit 510 based on the orientation of the X-ray radiation unit 510 and the orientation of the X-ray detector 600, so that the X-ray radiation unit 510 and the X-ray detector 600 face each other.

The main control unit 520 of the X-ray apparatus 500 may select the X-ray detector 600 to be used for photographing based on orientation information of the X-ray radiation unit 510 and orientation information of the X-ray detector 600.

For example, a main control unit 520 of an X-ray apparatus 500 may control orientation of an X-ray radiation unit 510 so that the X-ray radiation unit 510 and a selected X-ray detector may face each other, based on orientation information of the selected X-ray detector.

The main control unit 520 of the X-ray apparatus 500 may determine whether the X-ray radiation unit 510 and the X-ray detector 600 face each other, based on orientation information of the X-ray radiation unit 510 and orientation information of the X-ray detector 600.

In this case, if the X-ray radiation unit 510 and the X-ray detector 600 don't face each other, a main control unit 520 of an X-ray apparatus 500 may control orientation of an X-ray radiation unit 510 or orientation of the X-ray detector 600 so that the X-ray radiation unit 510 and a selected X-ray detector may face each other.

For example, orientation information of the X-ray radiation unit 510 includes at least one of selected from position information of the X-ray radiation unit 510 and directional information of the X-ray radiation unit 510 and orientation information of an X-ray detector includes at least one of selected from position information of the X-ray detector and directional information of the X-ray detector.

In this case, the position of the X-ray radiation unit may be controlled based on the position information of the selected X-ray detector, and the direction of the X-ray radiation unit may be controlled based on the direction information of the selected X-ray detector. The direction of the X-ray radiation unit may be controlled based on the position information of the selected X-ray detector, and the position of the X-ray radiation unit may be controlled based on the direction information of the selected X-ray detector. The position and direction of the X-ray radiation unit may be simultaneously or sequentially controlled based on the position information and direction information of the selected X-ray detector.

The main control unit 520 of the X-ray apparatus 500 may control the position of the X-ray radiation unit 510 based on the position information of the X-ray detector 600.

For example, after the position of the X-ray detector is determined, the X-ray radiation unit may move to a position corresponding to the position of the X-ray detector in order to perform X-ray photographing. For example, the X-ray radiation unit may move to a position where a distance between the detector and the X-ray radiation unit is 100 cm or 180 cm.

The main control unit 520 of the X-ray apparatus 500 may control the directional of the X-ray radiation unit 510 based on the directional information of the X-ray detector 600.

For example, after the direction of the X-ray detector, namely, a direction in which the X-ray detector receives an X-ray, is determined, the main control unit of the X-ray system may control the direction of the X-ray radiation unit, namely, an X-ray radiation direction or an X-ray radiation angle, to be faced with the direction of the X-ray detector.

The embodiments of the present invention can be written as computer programs and can be implemented in general-use digital computers that execute the programs using a computer readable recording medium.

Examples of the computer readable recording medium include magnetic storage media (e.g., ROM, floppy disks, hard disks, etc.), optical recording media (e.g., CD-ROMs, or DVDs), etc.

The exemplary embodiments should be considered in descriptive sense only and not for purposes of limitation. Descriptions of features or aspects within each embodiment should typically be considered as available for other similar features or aspects in other embodiments.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An X-ray apparatus comprising:
   an X-ray radiation unit configured to radiate X-rays to an object; and
   a main control unit configured to acquire orientation information of the X-ray radiation unit and orientation information of an X-ray detector and select the X-ray detector based on the orientation information of the X-ray radiation unit and the orientation information of the X-ray detector;
   a communication unit configured to transmit a signal to the X-ray detector in response to the X-ray detector being selected based on the orientation information of the X-ray radiation unit and the orientation information of the X-ray detector,
   wherein the signal is a prepare signal which is generated in the main control unit to prepare the selected X-ray detector to receive the X-rays.

2. The X-ray apparatus of claim 1, wherein the signal is generated based on the orientation information of the X-ray radiation unit and the orientation information of the X-ray detector.

3. The X-ray apparatus of claim 1, wherein the signal is generated based on a user's input.

4. The X-ray apparatus of claim 1, wherein the X-ray detector, which has been selected, is a first X-ray detector of a plurality of X-ray detectors, and
   wherein the main control unit is configured to acquire respective pieces of orientation information of the plurality of X-ray detectors and to further select a second X-ray detector among the plurality of X-ray detectors based on the orientation information of the X-ray radiation unit and the respective pieces of orientation information of the plurality of X-ray detectors.

5. The X-ray apparatus of claim 4, further comprising:
   an output unit configured to display information about at least one of the first X-ray detector and the second X-ray detector that is selectable by a user; and
   an input unit configured to receive a user's input configured to select one of the first X-ray detector and the second X-ray detector from the information displayed on the output unit,
   wherein the main control unit is configured to select one of the first X-ray detector and the second X-ray detector, based on the user's input.

6. The X-ray apparatus of claim 5, wherein the main control unit is configured to arrange the information about at least one of the first X-ray detector and the second X-ray detector according to a predetermined arrangement criterion, and control the output unit to display the arranged information.

7. The X-ray apparatus of claim 1, wherein the communication unit is configured to receive information related to orientation of the X-ray detector, from the X-ray detector, and
   wherein the main control unit is configured to acquire the orientation information of the X-ray detector, based on a reference orientation information of the X-ray detector and the received information.

8. The X-ray apparatus of claim 7, wherein the reference orientation information is reset in response to coupling the X-ray detector to a stand receptor or a table receptor.

9. The X-ray apparatus of claim 1, wherein the main control unit is configured to control orientation of the X-ray radiation unit, based on the orientation information of the X-ray detector.

10. The X-ray apparatus of claim 1, wherein the orientation information of the X-ray radiation unit comprises position information of the X-ray radiation unit, and the orientation information of the X-ray detector comprises position information of the X-ray detector, and
wherein the main control unit is configured to select the X-ray detector when a difference between the position information of the X-ray radiation unit and the position information of the X-ray detector is included in a predetermined range.

11. The X-ray apparatus of claim 10, wherein the position information of the X-ray radiation unit comprises a position vector of the X-ray radiation unit in a global coordinate system expressed as an inertial frame in which an arbitrary location within an X-ray photographing space designated as an origin, and
wherein the position information of the X-ray detector comprises a position vector of the X-ray detector in the global coordinate system.

12. The X-ray apparatus of claim 11, wherein the main control unit is configured to select the X-ray detector, based on a relative vector that is a difference between the position vector of the X-ray radiation unit and the position vector of the X-ray detector.

13. The X-ray apparatus of claim 1, wherein the orientation information of the X-ray radiation unit comprises directional information of the X-ray radiation unit and the orientation information of the X-ray detector comprises directional information of the X-ray detector, and
wherein the main control unit is configured to select the X-ray detector when a difference between the directional information of the X-ray radiation unit indicating a directional orientation of the X-ray radiation unit and the directional information of the X-ray detector indicating a facing direction of the X-ray radiation unit, is included in a predetermined range.

14. The X-ray apparatus of claim 13, wherein the directional information of the X-ray radiation unit comprises a first normal vector on a surface of the X-ray radiation unit, and
wherein the directional information of the X-ray detector comprises a second normal vector perpendicular to a surface of the X-ray detector.

15. The X-ray apparatus of claim 14, wherein the main control unit is configured to select the X-ray detector corresponding to the second normal vector when a difference between angles of the first normal vector and the second normal vector is included in a predetermined range.

16. A wireless X-ray detector comprising:
a sensor unit configured to sense orientation of the wireless X-ray detector;
an X-ray detecting unit configured to convert an X-ray into an electric signal;
a communication unit configured to transmit orientation information of the wireless X-ray detector to an X-ray apparatus; and
a control unit configured to control the communication unit to transmit the orientation information to the X-ray apparatus, and to receive a control signal from the X-ray apparatus after the orientation information has been transmitted,
wherein the control signal is a prepare signal which is generated in the X-ray apparatus to activate the X-ray detector to receive the X-ray, based on the orientation information.

17. The wireless X-ray detector of claim 16, wherein the control unit is configured to acquire the orientation information of the wireless X-ray detector, based on the orientation of the wireless X-ray detector sensed by the sensor unit.

18. The wireless X-ray detector of claim 16, wherein the orientation information of the wireless X-ray detector is reset in response to coupling the wireless X-ray detector to a stand receptor or a table receptor.

19. The wireless X-ray detector of claim 16, wherein the control signal is generated based on a user's input.

20. The wireless X-ray detector of claim 16, wherein the control signal is generated based on orientation information of an X-ray radiation unit and the orientation information of the wireless X-ray detector.

21. The wireless X-ray detector of claim 20, wherein the orientation information of the X-ray radiation unit comprises position information of the X-ray radiation unit,
the orientation information of the wireless X-ray detector comprises position information of the wireless X-ray detector, and
the control signal is generated when a difference between the position information of the X-ray radiation unit and the position information of the wireless X-ray detector is included in a predetermined range.

22. The wireless X-ray detector of claim 21, wherein the position information of the X-ray radiation unit comprises a position vector of the X-ray radiation unit in a global coordinate system expressed as an inertial frame in which an arbitrary location within an X-ray photographing space is designated as an origin, and
wherein the position information of the wireless X-ray detector comprises a position vector of the wireless X-ray detector in the global coordinate system.

23. The wireless X-ray detector of claim 22, wherein the control signal is generated based on a relative vector that is a difference between the position vector of the X-ray radiation unit and the position vector of the wireless X-ray detector.

24. The wireless X-ray detector of claim 20, wherein the orientation information of the X-ray radiation unit comprises directional information of the X-ray radiation unit and the orientation information of the wireless X-ray detector comprises directional information of the wireless X-ray detector, and
wherein the control signal is generated when a difference between the directional information of the X-ray radiation unit indicating a directional orientation of the X-ray radiation unit and the directional information of the wireless X-ray detector indicating a facing direction of the X-ray radiation unit, is included in a predetermined range.

25. The wireless X-ray detector of claim 24, wherein the directional information of the X-ray radiation unit comprises a first normal vector on a surface of the X-ray radiation unit, and
wherein the directional information of the wireless X-ray detector comprises a second normal vector perpendicular to a surface of the wireless X-ray detector.

26. The wireless X-ray detector of claim 25, wherein the control signal is generated when a difference between angles of the first normal vector and the second normal vector is included in a predetermined range.

27. An X-ray apparatus comprising:
- an X-ray radiation unit configured to radiate X-rays to an object; and
- a control unit configured to acquire orientation information of the X-ray radiation unit and orientation information of an X-ray detector, and to determine whether the X-ray radiation unit and the X-ray detector face each other,
- wherein the orientation information of the X-ray detector is received from the X-ray detector that senses its own orientation as at least one of a moving direction, a moving angle, and a moving distance of the X-ray detector based on initial orientation information of the X-ray detector.

28. The X-ray apparatus of claim 27, wherein the X-ray detector is configured to sense its own orientation with at least one of a gyroscope, an inertial measurement unit (IMU), an accelerometer, a GPS, and a magnetometer installed in the X-ray detector.

29. The X-ray apparatus of claim 27, wherein the initial information of the X-ray detector is determined by coupling of the X-ray detector to a stand receptor or a table receptor.

30. The X-ray apparatus of claim 1, wherein the X-ray detector is configured to transmit a ready signal, to the communication unit, in response to the X-ray detector completing its activation.

* * * * *